(12) United States Patent
Tan et al.

(10) Patent No.: US 9,046,526 B2
(45) Date of Patent: Jun. 2, 2015

(54) METHOD FOR DETERMINING PROTEIN-NUCLEIC ACID INTERACTION

(75) Inventors: Yen Nee Tan, Singapore (SG); Xiaodi Su, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days.

(21) Appl. No.: 13/377,819

(22) PCT Filed: May 27, 2010

(86) PCT No.: PCT/SG2010/000196
§ 371 (c)(1),
(2), (4) Date: Mar. 5, 2012

(87) PCT Pub. No.: WO2010/144053
PCT Pub. Date: Dec. 16, 2010

(65) Prior Publication Data
US 2012/0156804 A1    Jun. 21, 2012

Related U.S. Application Data

(60) Provisional application No. 61/186,476, filed on Jun. 12, 2009.

(51) Int. Cl.
*G01N 33/553* (2006.01)
*G01N 33/68* (2006.01)
(Continued)

(52) U.S. Cl.
CPC ............ *G01N 33/6803* (2013.01); *G01N 33/74* (2013.01); *G01N 33/54346* (2013.01); *G01N 33/539* (2013.01); *G01N 33/587* (2013.01); *C12Q 2565/113* (2013.01)

(58) Field of Classification Search
CPC ..... G01N 33/74; G01N 33/82; G01N 33/587; C12Q 2565/113
See application file for complete search history.

(56) References Cited

U.S. PATENT DOCUMENTS 4,313,734 A * 2/1982 Leuvering ...................... 436/525
7,122,384 B2 * 10/2006 Prober et al. .................. 436/524
(Continued)

FOREIGN PATENT DOCUMENTS

| EP | 1 584 914 A1 | 10/2005 | |
|---|---|---|---|
| WO | WO 2008/073175 A2 * | 6/2008 | .............. C12M 3/00 |
| WO | WO 2009/018576 A1 | 2/2009 | |

OTHER PUBLICATIONS

Wei, H et al., "Simple and sensitive aptamer-based colorimetric sensing of proteine using unmodified gold nanparticle probes", Chem. Commun. (2007) 36:3735-3737.*

(Continued)

*Primary Examiner* — Bao Thuy L Nguyen
*Assistant Examiner* — Gary E Hollinden
(74) *Attorney, Agent, or Firm* — Blakely, Sokoloff, Taylor & Zafman LLP

(57) ABSTRACT

The present invention refers to a method of determining protein-nucleic acid interaction. The method comprises mixing a protein with a sample comprising a nucleic acid which is suspected to interact with the protein to form a first mixture. The first mixture can be incubated to allow interaction between the protein and nucleic acid. Metallic nanoparticles are added to the first mixture to obtain a second mixture. An electrolyte is added to the first or second mixture to determine the protein-nucleic acid interaction. The present invention also refers to a kit for determining protein-nucleic acid interaction. The kit comprises a protein capable of interacting with a nucleic acid or a nucleic acid capable of interacting with a protein, and at least one type of metallic nanoparticle.

18 Claims, 9 Drawing Sheets

(51) Int. Cl.
*G01N 33/543* (2006.01)
*G01N 33/539* (2006.01)
*G01N 33/74* (2006.01)
*G01N 33/58* (2006.01)

(56) References Cited

U.S. PATENT DOCUMENTS

| | | | | |
|---|---|---|---|---|
| 7,235,361 | B2* | 6/2007 | Bawendi et al. | 506/17 |
| 8,026,108 | B1* | 9/2011 | Huo et al. | 436/525 |
| 8,304,256 | B2* | 11/2012 | Frederix et al. | 436/518 |
| 8,617,907 | B2* | 12/2013 | Birch et al. | 436/525 |
| 2002/0132371 | A1* | 9/2002 | Kreimer et al. | 436/525 |
| 2003/0108987 | A1* | 6/2003 | Rothman et al. | 435/69.1 |
| 2003/0211488 | A1* | 11/2003 | Mirkin et al. | 435/6 |
| 2004/0110154 | A1* | 6/2004 | Baxter et al. | 435/6 |
| 2004/0253648 | A1* | 12/2004 | Fletterick et al. | 435/7.2 |
| 2005/0221507 | A1* | 10/2005 | Koo et al. | 436/525 |
| 2005/0266449 | A1* | 12/2005 | Kugler et al. | 435/6 |
| 2006/0177855 | A1* | 8/2006 | Utermohlen et al. | 436/514 |
| 2007/0155021 | A1* | 7/2007 | Zhang et al. | 436/518 |
| 2010/0062545 | A1* | 3/2010 | Geddes | 436/525 |
| 2010/0311605 | A1* | 12/2010 | Lin et al. | 506/9 |
| 2011/0294135 | A1* | 12/2011 | Carlson | 435/6.15 |
| 2012/0070909 | A1 | 3/2012 | Su et al. | |

OTHER PUBLICATIONS

Kanjanawarut, R. et al., "Colorimetric detection of DNA using umodified metallic nanoparticles and peptide nucleic acid probes", Analytical Chemistry (2009) 81:6122-6129.*

Li H. et al., "Colorimetric detection of DNA sequences based on electrostatic interactions with unmodified gold nanoparticles", PNAS (2004) 101(39):14036-14039.*

Sato, K. et al., "Non-cross-linking gold nanoparticle aggregation as a detection method for single-base substitutions", Nucleic Acids Research (2005) 33(1):e4.*

Li, Y et al., "Heme protein assisted dispersion of gold nanoparticle multilayers on chips: from stabilization to high-denisty double-stranded DNAs fabricated in situ for protein/DNA binding", Analytical Chemistry (2009) 81(10):4076-4081.*

Su, X et al., "Combinational application of surface plasmon resonance spectroscopy and quartz crystal microbalance for studying nulear hormone receptor-response element interactions" Analytical Chemistry (2006) 78(15):5552-5558.*

Tasset, D.M. et al., "Oligonucleotide inhibitors of human thrombin that bind distinct epitopes", J. Molecular Biology (1997) 272:688-698.*

PCT International Search Report for PCT Counterpart Application No. PCT/SG2010/000196, 5 pgs., (Aug. 23, 2010).

PCT Written Opinion of the International Searching Authority for PCT Counterpart Application No. PCT/SG2010/000196, 6 pgs., (Aug. 23, 2010).

PCT International Preliminary Report on Patentability (Chapter II of the Patent Cooperation Treaty) for PCT Counterpart Application No. PCT/SG2010/000196, 12 pgs., (Jul. 15, 2011).

Bin Liu, et al., "Characterization of TectoRNA Assembly with Cationic Conjugated Polymers", J. Am. Chem. Soc., vol. 126, pp. 4076-4077, (2004).

Katherine C. Grabar, et al., "Preparation and Characterization of Au Colloid Monolayers", Anal. Chem., vol. 67, pp. 735-743, (1995).

Leon Maya, et al., "Assembly of Gold Nanoclusters on Silicon Surfaces", Langmuir, vol. 18, pp. 2392-2397, (2002).

Yen Nee Tan, et al., "Aspartic Acid Synthesis of Crystalline Gold Nanoplates, Nanoribbons, and Nanowires in Aqueous Solutions", J. Phys. Chem. C, vol. 112, pp. 5463-5470, (2008).

Huey Fang Teh, et al., "Characterization of Protein—DNA Interactions Using Surface Plasmon Resonance Spectroscopy with Various Assay Schemes", Biochemistry, vol. 46, pp. 2127-2135, (2007).

Yen Nee Tan, et al., "Gold-Nanoparticle-Based Assay for Instantaneous Detection of Nuclear Hormone Receptor-Response Elements Interactions", Analytical Chemistry, vol. 82, No. 7, pp. 2759-2765, (Apr. 1, 2010).

* cited by examiner

FIG. 3 (cont)
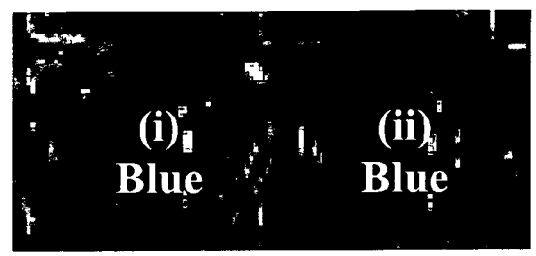
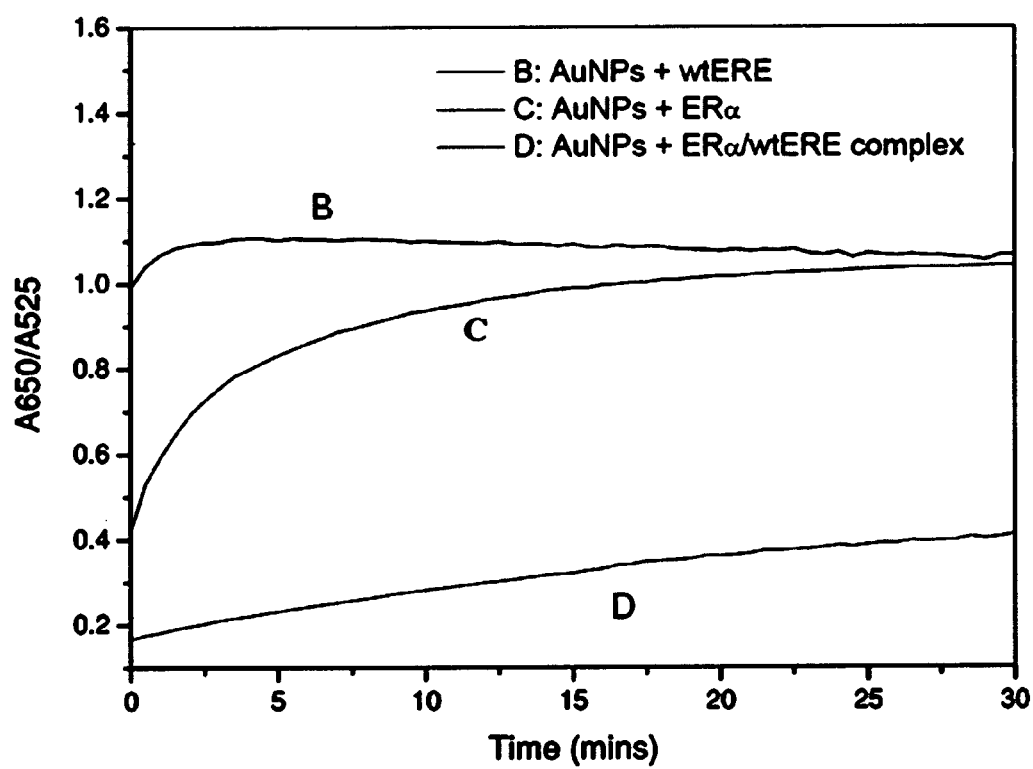
FIG. 4

FIG. 5

MTMTLHTKASGMALLHQIQGNELEPLNRPQLKIPLERPLGEVYLDSSKPAVYNYPE
GAAYEFNAAAAANAQVYGQTGLPYGPGSEAAAFGSNGLGGFPPLNSVSPSPLMLL
HPPPQLSPFLQPHGQQVPYYLENEPSGYTVREAGPPAFYRPNSDNRRQGGRERLAS
TNDKGSMAMESAKETRYCAVCNDYASGYHYGVWSCEGCKAFFKRSIQGHNDYM
CPATNQCTIDKNRRKSCQACRLRKCYEVGMMKGGIRKDRRGGRMLKHKRQRDD
GEGRGEVGSAGDMRAANLWPSPLMIKRSKKNSLALSLTADQMVSALLDAEPPILY
SEYDPTRPFSEASMMGLLTNLADRELVHMINWAKRVPGFVDLTLHDQVHLLECA
WLEILMIGLVWRSMEHPGKLLFAPNLLLDRNQGKCVEGMVEIFDMLLATSSRFRM
MNLQGEEFVCLKSIILLNSGVYTFLSSTLKSLEEKDHHRVLDKITDTLHLMAKAG
LTLQQQHQRLAQLLLILSHIRHMSNKGMEHLYSMKCKNVVPLYDLLLEMLDAHR
LHAPTSRGGASVEETDQSHLATAGSTSSHSLQKYYITGEAEGFPATV

FIG. 6

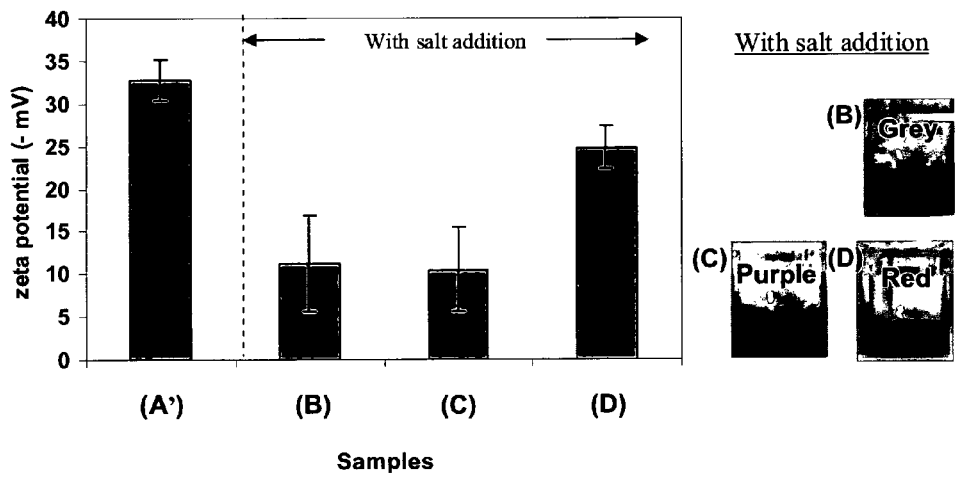

FIG. 10
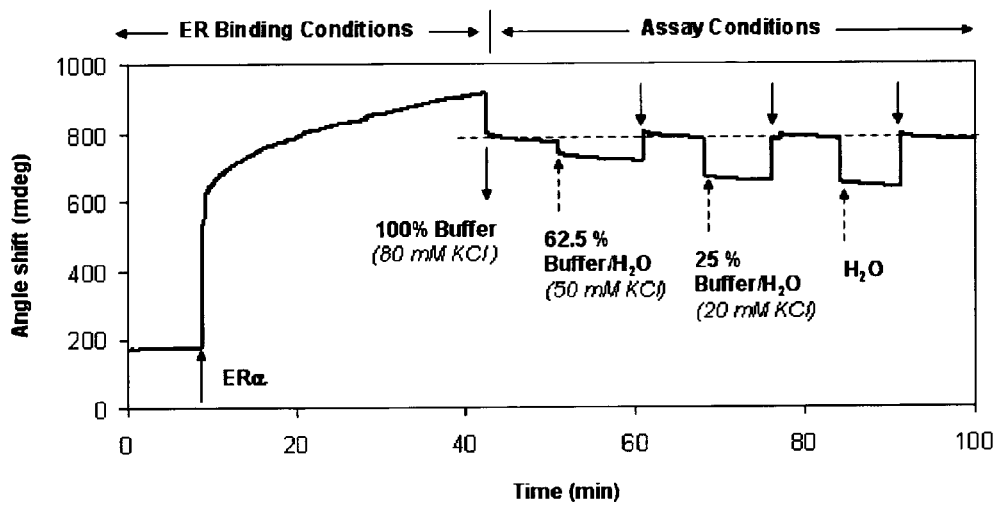
FIG. 11
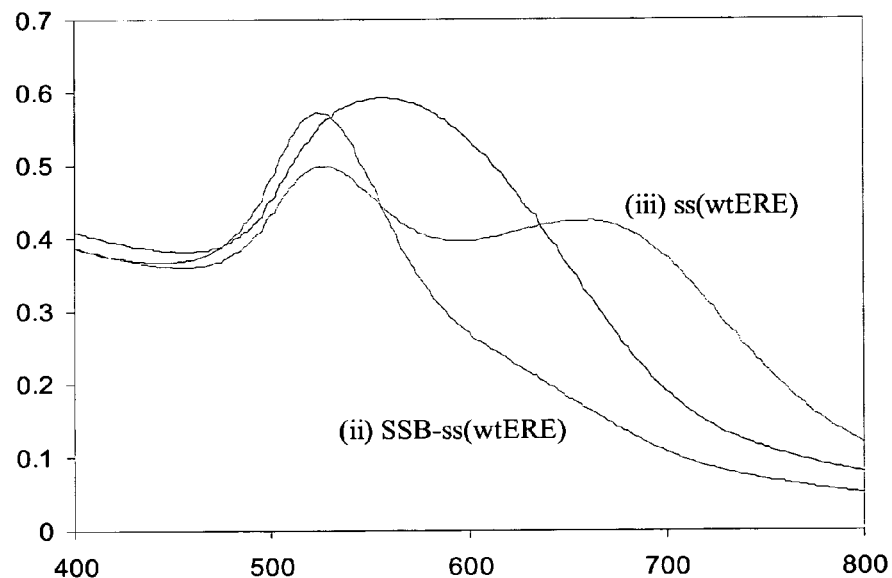
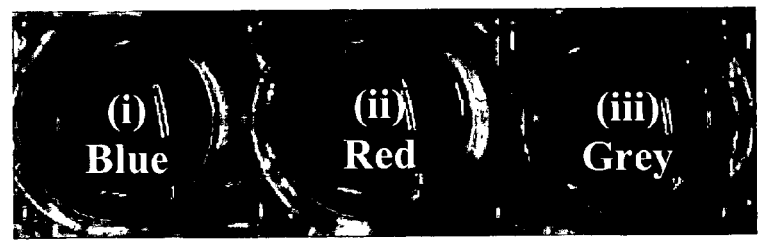

SEQUENCE LISTING

```
<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: wild-type ERE (wtERE)

<400> SEQUENCE: 1
```
gtccaaagtc aggtcacagt gacctgatca aagt                                34

<210> SEQ ID NO 2
<211> LENGTH: 34
<212> TYPE: DNA
<213> ORGANISM: Artificial Sequence
<220> FEATURE:
<223> OTHER INFORMATION: mutant ERE (mutERE)

<400> SEQUENCE: 2
gtccaaagtc agttcacagt gatctgatca aagt                                34

<210> SEQ ID NO 3
<211> LENGTH: 34
<212> TYPE: DNA
<213> ORGANISM: Artificial Sequence
<220> FEATURE:
<223> OTHER INFORMATION: non ERE (scrDNA)

<400> SEQUENCE: 3
gtccaaagtc aatcgccagc acgatgatca aagt                                34

<210> SEQ ID NO 4
<211> LENGTH: 34
<212> TYPE: DNA
<213> ORGANISM: Homo sapiens

<400> SEQUENCE: 4
tccccctgca aggtcacggt ggccaccccg tgag                                34

<210> SEQ ID NO 5
<211> LENGTH: 14
<212> TYPE: DNA
<213> ORGANISM: Artificial Sequence
<220> FEATURE:
<223> OTHER INFORMATION: ERE core sequence
<220> FEATURE:
<221> NAME/KEY: misc_feature
<222> LOCATION: (7)..(9)
<223> OTHER INFORMATION: n is a, c, g, or t

<400> SEQUENCE: 5
ggatcannnt gacc                                                      14

<210> SEQ ID NO 6
<211> LENGTH: 595
<212> TYPE: PRT
<213> ORGANISM: Homo sapiens

<400> SEQUENCE: 6

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His

```
            100                 105                 110
Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
            130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
                195                 200                 205

Phe Lys Arg Ser Ile Gln Gly His Asn Asp Tyr Met Cys Pro Ala Thr
            210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
                275                 280                 285

Ala Asn Leu Trp Pro Ser Pro Leu Met Ile Lys Arg Ser Lys Lys Asn
            290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
                435                 440                 445

Lys Ser Ile Ile Leu Leu Asn Ser Gly Val Tyr Thr Phe Leu Ser Ser
            450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
            515                 520                 525
```

```
Lys Cys Lys Asn Val Val Pro Leu Tyr Asp Leu Leu Leu Glu Met Leu
    530             535             540

Asp Ala His Arg Leu His Ala Pro Thr Ser Arg Gly Gly Ala Ser Val
545             550             555             560

Glu Glu Thr Asp Gln Ser His Leu Ala Thr Ala Gly Ser Thr Ser Ser
            565             570             575

His Ser Leu Gln Lys Tyr Tyr Ile Thr Gly Glu Ala Glu Gly Phe Pro
            580             585             590

Ala Thr Val
    595
```

METHOD FOR DETERMINING PROTEIN-NUCLEIC ACID INTERACTION

CROSS-REFERENCE TO RELATED APPLICATIONS

This patent application is a U.S. National Phase application under 35 U.S.C. 0371 International Application No. PCT/SG2010/000196, filed entitled METHOD FOR DETERMINING PROTEIN-NUCLEIC ACID INTERACTION which claims the benefit of priority of a U.S. provisional patent application for "Method to Measure Protein-DNA Interaction" filed on Jun. 12, 2009 with the United States Patent and Trademark Office, and there duly assigned Ser. No. 61/186,476. The content of said application filed on Jun. 12, 2009 is incorporated herein by reference in its entirety for all purposes.

INCORPORATION BY REFERENCE

This application incorporates by reference the material (i.e., Sequence Listing) in the ASCII text file named P104625_Sequence_Listing_ST25, created on Dec. 4, 2011 (modified Dec. 5, 2011), having a size in bytes of 6,386 bytes.

TECHNICAL FIELD

The present invention refers to the field of biochemistry and in particular to technologies concerning the determination of protein-nucleic acid interaction.

BACKGROUND

Many regulatory steps in cellular processes, such as replication and transcription, depend upon binding of proteins to specific nucleic acid sequences. Therefore, an understanding of sequence-dependent binding dynamics in protein-nucleic acid complexes is important for gene regulation. Conventional methods for studying protein-nucleic acid interactions include DNaseI footprinting assays, electrophoretic mobility shift assays (EMSA), enzyme linked immunosorbent assays (ELISA), genetic analysis and X-ray crystallography.

EMSA, also known as gel shift assay, is used extensively in modern molecular biology for studying protein-nucleic acid interaction. This technique, however, suffers from a number of disadvantages. Firstly, use of hazardous nucleic acid probes labeled with radioactive phosphate can result in environmental and safety issues. In addition, the assay procedures are time consuming and labor-intensive. Furthermore, building of the detection facilities such as radio protection lab is subjected to stringent requirements. These disadvantages render this technique less amendable for fast and robust detection of specific protein-nucleic interactions on large scale, which are vital attributes in modern genomic research.

Chip or biosensor-based techniques, such as surface plasmon resonance (SPR) spectroscopy and transcription factor (TF) ELISA kits (Panomics Inc. Denmark), eliminate use of biohazard labels. However, these methods suffer from other limitations in association with the 'solid-liquid phase' binding nature, such as requirement of complex surface chemistry for probe immobilization, slow inefficient binding between probe and surface of substrate, steric effects, and tedious procedure due to the numerous rinsing steps. In addition, equipments required for detection are often expensive.

In summary, current state of the art methods are not cost effective, and are inconvenient and inefficient for large scale screening of protein-nucleic acid interaction.

It is therefore an object of the present invention to provide an alternative method which can be used for determining protein-nucleic acid interactions which overcomes at least some of the above disadvantages.

SUMMARY OF THE INVENTION

In a first aspect, the invention provides a method of determining protein-nucleic acid interaction. The method comprises mixing a protein with a sample comprising a nucleic acid which is suspected to interact with the protein to form a first mixture. The first mixture can be incubated to allow interaction between the protein and nucleic acid. Metallic nanoparticles are added to the first mixture to obtain a second mixture. An electrolyte is added to the first or second mixture to determine the protein-nucleic acid interaction.

In a second aspect, the invention provides a kit for determining protein-nucleic acid interaction. The kit comprises a protein capable of interacting with a nucleic acid or a nucleic acid capable of interacting with a protein, and at least one type of metallic nanoparticle.

BRIEF DESCRIPTION OF THE DRAWINGS

The invention will be better understood with reference to the detailed description when considered in conjunction with the non-limiting examples and the accompanying drawings, in which:

FIG. 4 is a graph showing ratio A650/A525 as a function of time for sample (B) to (D). From the graph, it can be seen that the time at which gradient of the curve decreases is different among the tested samples, with sample (D) being the slowest, followed by sample (C), and sample (B). Therefore, AuNPs in the presence of ERα-wtERE complex i.e. sample (D) underwent the least and/or slowest aggregation upon salt addition, followed by sample (C), and lastly sample (B).

FIG. 5 shows a ERα sequence (Sequence ID No. 6). In the figure, the positively charged amino acid residues, i.e. lysine (K), histidine (H) and arginine (R) that may affect the charge property of the AuNPs are highlighted in grey. Cysteine (C) and histidine (H) residues that could be responsible for the protein binding to AuNPs are underlined. The mutual compensation between these two effects (electrostatic destabilization and steric stabilization) eventually leads to the intermediate particle stability observed.

FIG. 6 is a graph comparing zeta potential of sample (A') to (D), wherein (A') is a solution containing bare AuNPs (i.e. with no addition of salt or biomolecules), (B) a salt solution containing AuNPs and 50 nM wtERE, (C) is a salt solution containing AuNPs and 100 nM ERα, and (D) is a salt solution containing AuNPs and ERα/wtERE complex (preincubated for 30 minutes in a buffer solution using 100 nM ERα and 50 nM wtERE). The zeta potential of sample (A') to (D) is (−32.82±2.43 mV), (−11.29±5.65 mV), (−10.55±4.90 mV) and (−24.04±6.45 mV) respectively. Also shown are photographs of sample (B) to (D) upon salt addition, in which (B) is grey, (C) is purple and (D) is red.

FIG. 10 is a SPR sensorgram showing binding of ERα (prepared in Tris-HCl buffer solution containing 80 mM KCl, 0.15 mM EDTA, 0.3 mM DTT and 1% of glycerol) to the immobilized ERα-wtERE on gold chip, followed by exchanges between protein binding buffer and AuNPs aggregation buffers. The down arrows indicate the time when the surface is rinsed with the protein binding buffer (80 mM KCl). The dash arrows indicate the time when diluted buffer containing low concentration of KCl (20 or 50 mM KCl) is applied. From the graph, a reversible buffer effect due to bulk refractive index change was observed.

FIG. 11 is a graph showing UV vis spectra of AuNPs exposed to other protein-DNA systems, i.e. single-stranded binding protein (denoted as SSB), single-stranded binding protein with single stranded wtERE (denoted as SSB-ss(wtERE)) and single stranded wtERE (denoted as ss(wtERE)). SSB-ss(wtERE) complex was preincubated in 10 mM Tris-HCl buffer solution (pH 7.4), containing 80 mM KCl, 0.15 mM EDTA, 0.3 mM DTT and 1% of glycerol before subjecting to colorimetric testing (final KCl concentration is 20 mM). Also shown is a photograph taken of the sample solutions 10 mins after salt was added. Sample SSB is blue, SSB-ss(wtERE) is red and ss(wtERE) is grey.

DETAILED DESCRIPTION OF THE INVENTION

Figure 1A:
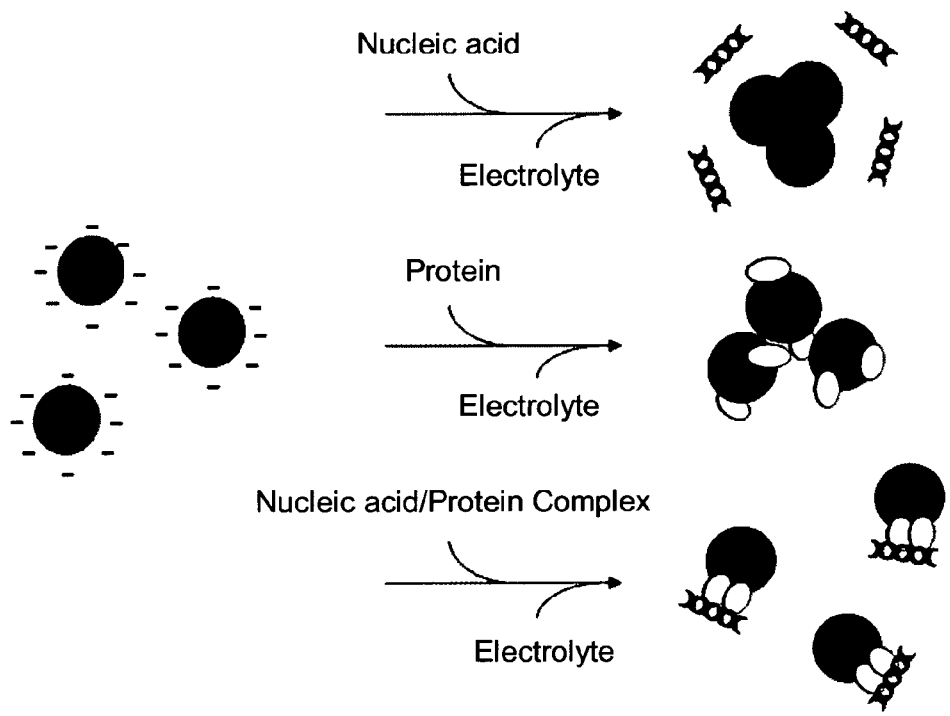
FIG. 1A illustrates the principle for determining protein-nucleic acid interaction according to an embodiment of the present invention. As shown in the figure, negatively charged metallic particles are stabilized in solution as the particles repel each other and thus avoid aggregation, leading to well dispersed particles in solution. This stabilization is a form of electrostatic stabilization, in which attractive van der Waals forces between the particles are counterbalanced by repulsive Coulomb forces acting between them. The solution containing well dispersed metallic particles only is red in color, which is used as a starting point to determine protein-nucleic acid interaction. Depending on the type of protein and/or nucleic acid that is made to contact with the solution, a color change can occur upon addition of an electrolyte, such as a salt. This is due to differences in extent at which the metallic particles are destabilized by the electrolyte in the presence of the protein and/or nucleic acid, which is affected by the binding affinity of the protein and nucleic acid in each mixture. This in turn affects degree of aggregation of the particles. Generally, the closer the particles are to each other, i.e. the higher the degree of aggregation, the lower the stability of the particles. For example, for a solution containing negatively charged metallic particles only, addition of an electrolyte causes the particles to lose their electrostatic stabilization force resulting in aggregation of the metallic particles. In an another example, when only a nucleic acid such as a double-stranded DNA (dsDNA) is added to the negatively charged metallic particles, the dsDNA is not able to bind to the particles due to its double helical structure which exposes highly charged repulsive backbone and prevents adsorption on the negatively charged particles. Therefore, upon addition of an electrolyte, the dsDNA is not able to stabilize the metallic particles and aggregation of the particles takes place. In another example, when only a protein is added to the negatively charged metallic particles, at certain pH conditions, the protein is slightly positively charged and is able to adsorb on the negatively charged particles. Therefore, upon addition of an electrolyte, the protein provides a steric barrier to prevent aggregation of the particle. The mutual compensation between electrostatic destabilization and steric stabilization of the protein on the particles leads to an intermediate particle stability. In a further example, when a protein-nucleic acid complex is added to the negatively charged metallic particles, the protein-nucleic acid can be bounded to the particle via one or more side chain present on the amino acid of the protein. The larger molecular size of the complex provides a more effective steric stabilization compared to the protein alone. In addition, the particles are well dispersed i.e. stabilized due to repulsion of the highly charged repulsive backbone on the nucleic acid present on the particles. Also, the degree of aggregation of the negative charged metallic particles depends on the binding affinity of the protein and nucleic acid. Generally, a higher binding affinity of the protein and nucleic acid results in a higher stabilization effect, thereby resulting in a lower degree of aggregation of the metallic particles. This system is even usable to detect subtle differences in protein-nucleic acid binding affinity.

This invention is based on the finding that interaction between a protein and nucleic acid, such as protein-nucleic acid complex, can stabilize negatively charged metallic nanoparticles against electrolyte-induced aggregation to a larger extent compared to either the protein or the nucleic acid alone. It has been shown that degree of aggregation of the metallic nanoparticles is dependent on binding affinity between the protein and the nucleic acid. The extent of stabilization is sequence dependent, and can distinguish a single base variation in the nucleic acid based on differences between the binding affinity. In addition, parameters of protein-nucleic acid binding events, such as sequence selectivity, nucleic acid binding properties of protein subtype, binding stoichiometry and sequence independent transient binding, can be determined using a method according to the present invention.

In a first aspect the present invention refers to a method of determining protein-nucleic acid interaction. The term "determine" refers to any qualitative and quantitative identification, such as identification presence or absence of a protein-nucleic acid interaction, the strength of interaction, or amount of interaction can be determined using the method described herein. Quantitative identification as used herein can be carried out via correlation of properties with that of a known sample. For example, quantitative identification of protein-nucleic acid interaction such as amount of interaction can be determined with reference to the corresponding amount of interaction of the sample.

The term "interaction" refers to the properties of binding or attraction between two entities. It refers to any kind of chemical bonding such as covalent bond, hydrogen or ionic bond, and any kind of physical bonding such as dipole dipole, hydrophobic interaction or Van der Waals forces. Accordingly, the term "protein-nucleic acid interaction" refers to the properties of binding or attraction between a protein and a nucleic acid.

As used herein, the terms protein, peptide and polypeptide are used interchangeably. Proteins referred to herein are proteins having nucleic acid binding capacity. Such proteins can be found in almost every known protein class. Therefore, for purposes of this application, a protein refers to proteins, protein fragments, peptides, oligopeptides and polypeptides. Proteins belong to the broad class of polypeptides, and refer to organic compounds molecules containing more than one amino acid (which include native and non-native amino acid monomers). Amino acids are molecules containing at least one carboxyl group (—COOH) and one amine (—NH$_2$) group. A side chain is present on the amino acid molecule, which can affect properties such as polarity and acid-base properties of the amino acid. The side chain can vary in size from a hydrogen atom in glycine, to a phenyl group in phenylalanine. Further examples of amino acids include aspartic acid, glutamic acid, arginine, lysine, asparagine, glutamine, alanine, tryptophan as well as any non-standard amino acid, such as selenocysteine, lanthionine, 2-aminoisobutyric acid, dehydroalanine or gamma-aminobutyric acid; or amino acid derivatives, such as 5-hydroxytryptophan or L-dihydroxyphenylalanine. Therefore, a protein molecule is made from a long chain of these amino acids, each linked to its neighbor through a covalent peptide (—CONH—) bond.

Proteins can be classified into five major categories, i.e. structural proteins, catalytic proteins, transport proteins, protective proteins, and regulatory proteins. Structural proteins refer to proteins that maintain structures of other biological components, like cells and tissues. Examples of structural proteins include, but are not limited to, collagen, keratin, elastin, sklerotin, and fibroin. Catalytic proteins refer to proteins that catalyze chemical and biochemical reactions within and outside of living cell. An example of catalytic protein is enzyme. Transport proteins refer to proteins that functions to convey molecules into and out of a cell, as well as transportation of molecules intracellularly. Examples of transport proteins include, but are not limited to, hemoglobin and serum albumin. Protective proteins refer to proteins that have the ability to protect other proteins from damage. In general, protective proteins function by minimizing degradation via conformational changes and enzymatic cleavage or digestion, thereby enhancing cell viability in the cells, tissues and organizations from which they are derived. Examples of protective proteins include, but are not limited to antibodies and thrombin. Regulatory proteins refer to proteins that bind to specific regulatory sequences of nucleic acids and act to switch genes on and off and thereby regulate the transcription of genes. Examples of regulatory proteins include, but are not limited to, hormones such as estrogen, adrenalin, insulin, growth hormone, steroid hormone, and thyroid hormone.

Proteins can be produced by living cells, and the activities of all living cells are conducted primarily by the thousands of different types of proteins each cell produces. The blueprint or code for synthesizing each protein can be found in a corresponding gene, i.e. each gene encodes the information needed to synthesize a specific protein. Gene expression can result in production of the protein, by transcription of the gene by RNA polymerase to produce a messenger RNA (mRNA) that contains the same protein-encoding information, and translation of the mRNA by ribosomes to produce the protein. The term "transcription" refers to the process of copying a DNA sequence of the gene by RNA polymerase into the mRNA, using the DNA as a template. The term "translation" refers to the process by which the information contained in the mRNA is used as a blueprint to synthesize the protein.

In some embodiments, the protein produced by living cells is a regulatory protein, such as hormone. In mammals, hormones can be synthesized in one organ or tissue, and can travel through the blood stream to various target organs. By interacting with specific receptor proteins, also known as nuclear receptors, in the target cells, the hormones can change the activities of the cell, for example, by changing the expression of specific genes, and the protein products of these genes then carry out the biological actions that result in altered cellular functions.

As used herein, the term "nuclear receptor" refers to a protein molecule found within a cell and which has ability to bind a ligand and to be incorporated into a nucleus of a cell. The term "ligand" as used herein refers to a substance or compound which can bind to the nuclear receptor, thereby creating a ligand/nuclear receptor complex, which in turn can bind to an appropriate response element and activate transcription therefrom. A response element (RE) refers to a region of a nucleic acid molecule, usually from a regulatory region of a gene that is capable of specifically binding to a binding protein, such as an activator molecule, for activation of transcription or for allowing elongation of a RNA transcript, or a repressor molecule, for inhibition of transcription. Therefore, ligand functions to modulate transcription of a nucleic acid maintained under control of a response element. Examples of ligand include, but are not limited to, hormones such as that described herein, and vitamins such as vitamin A and vitamin D.

Accordingly, the term "nuclear hormone receptor" refers to a nuclear receptor which has ability to bind with a hormone. Nuclear hormone receptors become active when they detect their respective corresponding hormone in the cellular environment. The term "corresponding hormone" refers to a specific hormone that binds to and activates a specific nuclear hormone receptor to regulate expression of a specific gene. Examples of nuclear hormone receptors and their corresponding hormones that have applications in the present invention include, but are not limited to, α and β isoforms of estrogen receptor (ER) having estradiol or estriol as a corresponding hormone, α and β isoforms of thyroid hormone receptor (TR) having thyroid hormone as a corresponding hormone, vitamin D receptor (VDR) having vitamin D as a corresponding hormone, α, β and γ isoforms of retinoic acid receptor (RAR) having trans-retinoic acid or 9-cis retinoic acid as a corresponding hormone, α, β and γ isoforms of retinoid X receptor (RXR) having retinoids (compounds related to retinoate, the carboxylate form of vitamin A) as a corresponding hormone, progesterone receptor (PR) having progesterone as a corresponding hormone, androgen receptor (AR) having testosterone as a corresponding hormone, glucocorticoid receptor (GR) having cortisol as a corresponding hormone, mineral corticoid receptor (MR) having aldosterone as a corresponding hormone, and α and γ isoforms of peroxisome proliferation-activated receptor (PPAR) having respectively Wy14643 and 15-deoxy-D-prostaglandin J2 as corresponding hormones.

In some embodiments, α and β isoforms of estrogen receptor (ER) are used as the nuclear hormone receptor. Estrogen receptors regulate estrogen gene expression by binding to specific DNA sequences known as estrogen response elements (EREs). The term "estrogen" as used herein refers to a substance, natural or synthetic, that exerts biological effects characteristic of estrogenic hormones, such as estradiol and equivalents thereof. Examples of estrogen hormones include 17-β-estradiol, α-estradiol, conjugated estrogens, esterified estrogens, micronized estradiol, sodium estrogen sulfate, ethinyl estradiol, estrone, and other estrogenic steroids and derivatives and esters thereof are representative of estrogens. Representative esters include estradiol-3,17-diacetate, estradiol-3-acetate, estradiol-17-acetate, estradiol-3,17-divalerate, estradiol-3-valerate, and estradiol-17-valerate.

The method according to the present invention comprises mixing a protein with a sample comprising a nucleic acid which is suspected to interact with the protein to form a first mixture. The method does not require that any of the molecules involved in the method is attached to a solid phase. All components used can be dispersed in a liquid or aqueous solution.

As used herein, the term "nucleic acid" refers to any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, DNA-RNA hybrid molecules and tecto-RNA molecules (e.g. Liu, B., et al., *J. Am. Chem. Soc.* (2004) 126, 4076-4077). DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, micro RNA having a length of between about 21 to 23 nucleotides etc. A respective nucleic acid may furthermore contain non-natural nucleotide analogues.

Many nucleotide analogues are known and can be present and/or used in the methods of the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

In some embodiments, the nucleic acid is a synthetic or naturally obtained DNA, RNA, DNA-RNA hybrid, or derivatives thereof. The nucleic acid can be negatively charged. For example, the nucleic acid can have a backbone that is negatively charged, such as a backbone containing a phosphodiester group. The nucleic acid used in the method of the present invention can be a double stranded DNA. Generally, the nucleic acid can be of any length, so long as it forms a complex with protein that is larger in size than either the nucleic acid or protein when taken alone. For example, the nucleic acid can have a length of between about 10 to 70 nucleotides, such as between about 10 to 30 nucleotides, or between about 20 to 50 nucleotides, or between about 30 to 60 nucleotides. In embodiments in which double stranded DNA (dsDNA) is used, length of the dsDNA is expressed in terms of base pairs instead of nucleotides. The nucleic acid can contain a response element capable of specifically binding to a protein, such as a nuclear receptor or a nuclear hormone receptor. In some embodiments, the nucleic acid comprises an estrogen response element (ERE).

The protein and sample comprising a nucleic acid which is suspected to interact with the protein can be mixed together in a suitable solvent, such as a buffer solution. All kinds of buffers can be used to conduct the method of the present invention therein, such as a tris(hydroxymethyl)aminomethane (TRIS) buffer, or a tris-hydrochloric acid buffer (TRIS-HCl), or a phosphate buffered saline (PBS), to name only a few. In one embodiment, the pH of the solution in which the method of the present invention is carried out is neutral (i.e. about pH 7). A neutral pH is used to mimic the physiological condition and to ensure good binding of the complex formed between protein and nucleic acid. Typically, the method of the present invention is carried out at room temperature.

In some embodiments, the protein and sample comprising a nucleic acid which is suspected to interact with the protein is incubated for a period of time so as to allow sufficient time for the protein and nucleic acid to interact. A suitable amount of time can be dependent on reaction conditions, such as the type of protein and nucleic acid, solvent used, temperature of solution, and amount of solution. Agitation, for example, by stirring, is not necessarily required to enhance interaction between the protein and nucleic acid, as this can cause the protein to become inactive. A person skilled in the art would be able to determine the appropriate amount of time for interaction to take place between the protein and nucleic acid. Typically, the amount of time for interaction to take place between the protein and nucleic acid is in the order of minutes, for example about 20 minutes, or about 30 minutes, or about 60 minutes.

The method according to the present invention comprises adding metallic nanoparticles to the first mixture, comprising the protein and the sample comprising a nucleic acid which is suspected to interact with the protein, such that a second mixture is formed. The metallic nanoparticles can be dispersed in the first mixture. In some embodiments, to enhance the measurability of these changes, the metallic nanoparticles are plasmonic nanoparticles. Plasmonic nanoparticles refer to metallic nanoparticles whose surface plasmon resonance frequency depends on the nanoparticle size, shape and composition. Light incident on plasmonic nanoparticles induces the conduction electrons in them to oscillate collectively with a certain resonant frequency. This resonant frequency changes in case the metallic nanoparticles aggregate and thus can be measured, e.g. with optical methods.

Manufacture of such plasmonic nanoparticles is known in the art (see e.g. Grabar, K. C., Freeman, R. G., et al., 1995, Anal. Chem., vol. 67, pp. 735). Such nanoparticles can be obtained in any known shape. For example, in some embodiments, the nanoparticles have a shape which is selected from the group consisting of a nanosphere, a nanocube, a nanorod, a nanotube, a nanostar, a nanocrescent, a nanoplate and mixtures thereof. With mixtures thereof it is meant that the nanoparticles used can include nanoparticles having not only a tubular shape but also nanoparticles having a plate like shape. In some embodiments, different nanoparticles with different shapes can be used.

Although silver and gold are the most commonly used materials for plasmonic nanoparticles, theoretically any metal, alloy or semiconductor with a large negative real dielectric constant and small imaginary dielectric constant can be used. In some embodiments, the nanoparticles are noble metal particles, alloys of noble metal particles or mixtures of materials referred to herein. Noble metal includes silver (Ag), palladium (Pd), gold (Au), platinum (Pt), iridium (Ir), osmium (Os), rhodium (Rh) and ruthenium (Ru). Examples of noble metal alloys include alloys of platinum and iridium, Pd—Pt, Pd—Rh or Pd—Pt—Rh, to name only a few. Other materials, such as aluminium, potentially offer advantages in refractive index sensitivity, different surface chemistries, and resonances into the ultraviolet, where many organic molecules absorb light. Copper can also be used as possible metal for the metallic nanoparticles.

In some embodiments, the metallic nanoparticles each have a size in at least one dimension of at least 10 nm or 20 nm or in a range of between about 10 nm to about 900 nm or in a range of between about 10 to 50 nm. In another example the size of the nanoparticles is in range of between about 10 to 30 nm, or about 20 to 30 nm.

The metallic nanoparticles can be well dispersed. In some embodiments, methods such as agitation or stirring can be used to disperse the metallic nanoparticles. In some embodiments, negatively charged metallic nanoparticles are used to avoid aggregation of the metallic nanoparticles prior to determination of protein-nucleic acid interaction. In some embodiments, the negatively charged metallic nanoparticles are metallic nanoparticles carrying a negative charge at nanoparticle surface.

Without wishing to be bound by theory, the inventors believe that the negatively charged metallic nanoparticles, which behave like colloidal particles, are stabilized in solution due to electrostatic stabilization. Electrostatic stabilization refers to the mechanism in which the attraction van der Waals forces between the particles are counterbalanced by the repulsive Coulomb forces acting between the negatively charged particles. In this mechanism, the particles can have an electric double layer, which is electrically neutral, and which consists of three parts. The first part called a surface charge layer is the negatively charged ions on the particle surface. The second part called a stern layer is made up of positive ions adsorbed on the particle surface due to electrostatic attraction. The third part comprises a diffuse layer made up of both positive and negative ions present in the solution. Presence of the electric double layer on the particles results in stabilization of the particles such that they do not aggregate. Depending on the type and extent of interaction between a protein and a nucleic acid, stability of the metallic nanoparticles can be changed.

Metallic nanoparticles with a negative surface charge can be nanoparticles wherein the negative charge of the metallic nanoparticles is conferred by a carboxylic acid or sulfonic acid or carbolic acid or a mixture of the aforementioned acids which is immobilized at the surface of the metallic nanoparticles.

In one embodiment, the carboxylic acid can be, but is not limited to citric acid, lactic acid, acetic acid, formic acid, oxalic acid, uric acid, pyrenedodecanoic acid, mercaptosuccinic acid, aspartic acid, to name only a few. Methods to immobilize such acids at the surface of metallic nanoparticles are known in the art. For example, citrate-stabilized AuNPs were prepared by thermal reduction of $HAuCl_4$ with sodium citrate (Grabar, K. C., Freeman, R. G., et al., 1995, supra). In brief, 500 mL of 1 mM $HAuAl_4$ was brought to a rolling boil with vigorous stirring. After that 50 mL of 38.8 mM sodium citrate was rapidly added, resulting in burgundy color. Boiling was continued for 10 min; the heating mantle was then removed, and stirring was continued for additional 15 min. Maya, L., et al. (2002, Langmuir, vol. 18, pp. 2392) discloses a method for immobilizing mercaptosuccinic acid at the surface of metallic nanoparticles. Tan, Y. N., et al., (2008, J. Phys. Chem. C, vol. 112, no. 14, pp. 5463) discloses a method for immobilizing aspartic acid at the surface of metallic nanoparticles.

The method according to the present invention comprises adding an electrolyte to the second mixture to determine the protein-nucleic acid interaction. The term "electrolyte" as used herein refers to ionic or molecular substances which, when in solution, break down or disassociate to form differently charged ions or differently charged particles. Addition of an electrolyte to the second mixture can compress the double layer around a metallic nanoparticle. When the double layer is compressed, the sphere of influence of the charges on the particle is reduced, allowing it to approach closer to another particle. This can allow the particles to combine, leading to aggregation of the metallic particles, which can show up as a change in color of the solution. Generally, stability of the solution is in the order of the following color sequence, i.e. red>purple>blue>grey, with red being the most stable and grey being the least stable. Examples of an electrolyte include, but are not limited to, an organic acid, an inorganic acid, a base, and a salt.

Non-limiting examples of an organic acid include carboxylic acids as described herein, sulphonic acids such as butanesulphonic acid, butanedisulphonic acid, benzenesulphonic acid, methylbenzenesulphonic acid, ethylbenzenesulphonic acid, dodecylbenzenesulphonic acid, 2,4,6-trimethylbenzenesulphonic acid, 2,4-dimethylbenzenesulphonic acid, 5-sulphosalicylic acid, 1-sulphonaphthalene, 2-sulphonaphthalene, hexanesulphonic acid, octanesulphonic acid and dodecanesulphonic acid, and amino acids such as glycine, alanine, valine, a-aminobutyric acid, Y-aminobutyric acid, alanine, taurine, serine, e-amino-nhexanoic acid, leucine, norleucine and phenylalanine. Non-limiting examples of an inorganic acid include hydrochloric acid, sulfuric acid, sulfurous acid, nitric acid, nitrous acid, phosphoric acid, boric acid and carbonic acid. Non-limiting examples of a base include potassium carbonate, calcium carbonate, sodium carbonate, barium carbonate, zinc carbonate hydroxide hydrate, magnesium carbonate hydroxide hydrate, calcium hydroxide, sodium hydroxide, magnesium hydroxide and aluminum hydroxide.

In some embodiments, the electrolyte is a salt. Suitable salts that can be used herein include any organic and inorganic salt. Organic salts are also known as polyelectrolytes or polysalts. Organic salt refers to a complex formed by charge attraction between oppositely charged polymers. Accordingly, organic salts are polymers comprising cationic and anionic components. An organic salt can be formed by any method well known in the art, such as by blending aqueous solutions containing the cationic polymer component and anionic polymer component, and allowing the charge interaction to occur. For example, the cationic polymer component can be a polyamine. Examples of polyamine includes $C_1$-$C_{12}$ dialkyl diallyl ammonium polymers, such as olydimethyl diallyl ammonium chloride, polydiethyl diallyl ammonium chloride, polydimethyl diallyl ammonium bromide, polydiethyl diallyl ammonium bromide, and poly(dimethyl diallyl ammonium chloride-co-acrylamide). For example, the anionic polymer component can be a carboxylic anionic polymer, a polysulfonic acid or an alginic acid.

An inorganic salt can be formed from the neutralization reaction of an acid and a base. Examples of inorganic salts include, but are not limited to NaCl, KCl, $CaCl_2$, $BaCl_2$, $MgCl_2$, NaBr, KBr, NaI, KBr, $NaNO_3$, $KNO_3$, $Mg(NO_3)_2$, $Ca(NO_3)_2$, $Na_2SO_4$, $K_2SO_4$, $NaClO_4$, $NH_4Cl$, $NH_4NO_3$, $(NH_4)_2SO_4$, $CH_3COONa$, $CH_3COONH_4$, to name only a few. At least one type of salt can be added. When two or more salts are added, they can be different types. For example, $Na_2SO_4$ can be added with NaCl. In some embodiments, KCl is used. KCl can dissociate in water to form a cation of $K^+$ and an anion of $Cl^-$. The concentration of the salt can be in the range of between about 0.01 M to about 0.5 M, or between about 0.01 M to about 0.25 M, or between about 0.01 M to about 0.1 M. The amount of salt required to induce particle aggregation can be determined using UV-vis spectroscopy, which is typically used to characterize particle aggregation extent through spectrum shift, such as that illustrated in Example 8.

The protein-nucleic acid interaction can be determined by degree of aggregation of the metallic nanoparticles. Degree of aggregation of the metallic nanoparticles referred to herein is dependent upon binding affinity between the protein and the nucleic acid. As used herein, "binding affinity" refers to strength of interaction between two entities. Binding affinity is sometimes referred to as $K_d$ or dissociation constant, which is an indication of the strength of binding between two entities in terms of how easy it is to separate them.

The disassociation constant can be determined by a variety of methods in which two separate entities are mixed together, the unbound portion is separated from the bound portion, and concentrations of unbound and bound are measured. For example, the unbound and bound portions may be separated from one another through adsorption, precipitation, gel filtration, dialysis, or centrifugation. The measurement of the concentrations of bound and unbound portions may be accomplished, for example, by spectroscopy or measuring parameters such as radioactivity or fluorescence. As used herein, a high binding affinity means that the dissociation constant for the complex is smaller than $1\times10^{-9}$ M. A low binding affinity means that the dissociation constant for the complex is greater or equal than $1\times10^{-3}$ M.

Typically, when the binding affinity between a protein and a nucleic acid is high, a complex is formed between the protein and the nucleic acid. In some embodiments, the protein-nucleic acid complex formed provides steric stabilization to the metallic nanoparticles, such that the particles are shielded from each other and hence do not aggregate upon addition of an electrolyte. In some embodiments, the protein-nucleic acid complex is formed from a protein containing one or more functional groups and a nucleic acid, such as a double stranded DNA. The double stranded DNA can be made up of a double helical structure which exposes highly charged repulsive phosphate backbone. The protein-nucleic acid complex can bind to the surface of the metallic nanoparticles through one or more functional groups present on the protein. Therefore, in addition to steric stabilization provided by the protein-nucleic acid complex bound on the particles, electrostatic stabilization is also provided as a result of the negative charge on the nucleic acid backbone, which prevents aggregation of particles upon addition of an electrolyte. The combination of the above two mechanisms, steric and electrostatic, to stabilize the nanoparticles is called electrosteric stabilization. A higher binding affinity between protein and nucleic acid can mean that more protein-nucleic acid complexes are formed, thereby providing greater stabilization of the metallic nanoparticles.

In some embodiments, the binding affinity between the protein and the nucleic acid is low. A lower binding affinity can mean that less protein-nucleic acid complexes are formed. In some embodiments, the nucleic acid can have one or more base sequence variation which is not perfectly recognized by the sequence-specific nucleic acid-binding protein. In some embodiments, the nucleic acid interacts with the protein only weakly such that weak and transient protein-nucleic acid complex is formed. In such instances, the protein and nucleic acid can provide lesser degree of stabilization of the metallic nanoparticles against aggregation.

Figure 1B:
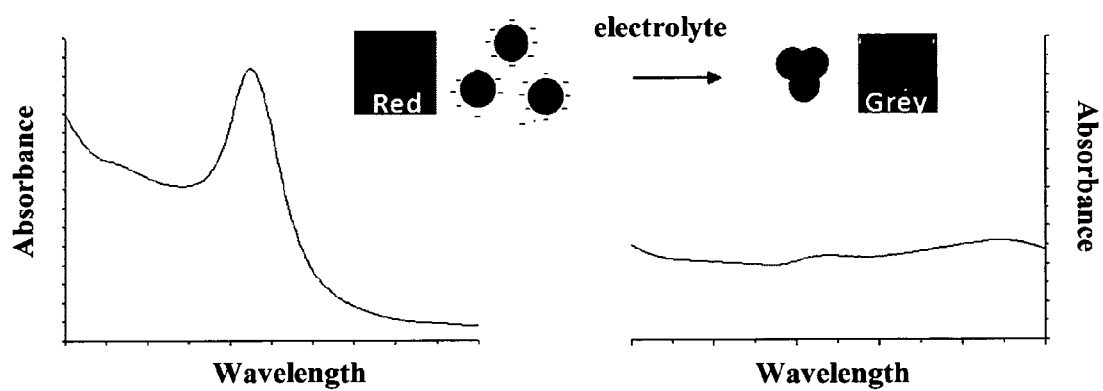
FIG. 1B is a schematic illustration of effects of electrolyte induced aggregation of metallic nanoparticles on ultraviolet visible spectroscopy (UV-vis) absorption spectrum according to an embodiment of the present invention. In the embodiment shown in FIG. 1B, gold nanoparticles are used, and salt is used as the electrolyte. The absorption curve profile of well dispersed gold nanoparticles, i.e. stabilized state, is different from that of aggregated gold nanoparticles, i.e. non stabilized state. Insert of the graphs are pictures showing corresponding change in degree of aggregation of gold nanoparticles (AuNPs), and photographs showing corresponding change in color of AuNPs from red to grey.

Generally, regardless of the binding affinity between protein and nucleic acid, the stabilization effect of a protein-nucleic acid complex is greater than protein or nucleic acid alone, due to a combination of steric and electrostatic stabilization i.e. electrosteric stabilization, compared to a solution containing protein or nucleic acid which can provide only steric or electrostatic stabilization. For example, when only a protein is added to the negatively charged metallic particles, at certain pH conditions, the protein is slightly positively charged and is able to adsorb on the negatively charged particles. Therefore, upon addition of an electrolyte, the protein provides a steric barrier to prevent aggregation of the particle. The mutual compensation between electrostatic destabilization and steric stabilization of the protein on the particles leads to an intermediate particle stability. For example, in embodiments wherein the nucleic acid is single stranded DNA, it can adsorb to the surface of AuNPs thereby providing electrostatic stabilization to the particles. In embodiments whereby the nucleic acid is dsDNA, it may not provide electrostatic stabilization to the AuNPs since it is prevented from adsorbing to the particle surface due to its double helix structure which exposes highly charged repulsive backbone and prevents adsorption on the negatively charged particles. FIG. 1A illustrates the principle for determining protein-nucleic acid interaction according to an embodiment of the present invention. FIG. 1B is a schematic illustration of effects of electrolyte induced aggregation of metallic nanoparticles on ultraviolet visible spectroscopy (UV-vis) absorption spectrum. Therefore, the method according to the present invention can be used to determine whether interaction takes place between protein and nucleic acid.

Not only can the method of the present invention be used to detect the presence or absence of protein-nucleic acid interaction, it can also be used to quantify the binding efficiency of protein-nucleic acid interaction. Depending on the binding efficiency of protein-nucleic acid interaction present in a sample compared to another sample, the degree of metallic particle aggregation will vary. A change of the degree of metallic particle aggregation will change for example the absorbance of the solution or the size of the metallic particle aggregate. This difference can be correlated to different binding efficiencies of protein-nucleic acid interaction present in the sample. To determine the exact binding efficiency of protein-nucleic acid interaction present in the sample the results obtained from a sample can be compared with the results of a sample comprising a known sequence specific nucleic acid binding to protein with high affinity. Methods to carry out such correlations are known in the art and include for example the generation of calibration curves obtained by measuring samples including a known sequence specific nucleic acid binding to protein with high affinity.

In some embodiments, the method of the present invention can be used to quantify the binding stoichiometry of protein-nucleic acid interaction. The term "binding stoichiometry" refers to the ratio of protein that is bound to nucleic acid. Binding stoichiometry of the protein that is bound to the nucleic acid can be determined by for example generating absorbance curves corresponding to different mole ratios of protein to nucleic acid, and comparing between the curves to determine the binding stoichiometry.

Upon addition of the electrolyte, the mixture can be incubated for a time period to allow binding of the nucleic acid, the protein or the protein-nucleic acid complex with the metallic nanoparticle. A suitable amount of time can be dependent on reaction conditions, such as the type of protein, nucleic acid and metallic nanoparticle, temperature of solution, and amount of solution. A person skilled in the art would be able to determine the appropriate amount of time for incubation. Typically, the amount of time required is in the order of minutes, for example about 20 minutes, or about 30 minutes, or about 60 minutes.

The electrolyte can also be added to the first mixture comprising a protein and a sample comprising a nucleic acid which is suspected to interact with the protein, followed by addition of the metallic nanoparticles to determine protein-nucleic acid interaction. In some embodiments, the electrolyte can be added to either the protein or the sample comprising a nucleic acid which is suspected to interact with the protein, prior to contacting the protein with the sample comprising a nucleic acid which is suspected to interact with the protein. Presence of an electrolyte, such as a salt can result in greater efficiency in protein-nucleic acid complex formation.

As previously mentioned, determining protein-nucleic acid interaction can be achieved by measuring the optical properties of the metallic nanoparticles or by measuring the size of the metallic nanoparticle aggregates formed. Aggregation changes for example the absorbance or the size caused by aggregation of multiple single nanoparticles. These changes can be measured using standard microscopic or spectroscopic methods. For example, optical properties such as absorbance can be determined with methods and devices known in the art, such as with a spectrophotometer. If the change of the optical properties is visible in the light wave range visible to humans, it is also possible to determine the differences with the naked eye. Using this method, determination of protein-nucleic interaction can be carried out in a simple and fast manner by observing color change in solution without the use of analytical instruments which can be expensive. The size of the nanoparticle aggregates which form upon interaction of a protein with a nucleic acid and induced by an electrolyte can be determined with transmission electron microscopy (TEM), or light scattering techniques or a coulter counter for small particles.

In addition, the binding efficiency of the protein-nucleic acid interaction can be determined by correlating the optical properties of the metallic nanoparticles or the size of metallic nanoparticle aggregates in one sample with the optical properties or size of metallic nanoparticle aggregates of another sample, wherein the other sample comprises a known specific or sequence-specific nucleic acid binding to protein with high affinity.

In a second aspect, the invention provides a kit for determining protein-nucleic acid interaction. The kit comprises a protein capable of interacting with a nucleic acid or a nucleic acid capable of interacting with a protein, and at least one type of metallic nanoparticle.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

In the experiments, an estrogen receptor/estrogen response element (ER/ERE) system was chosen as a model because it is of great biological and practical importance. The term "estrogen receptors" refer to are DNA-binding proteins that belong to the nuclear receptor superfamily of transcriptional factors. ERs regulate estrogen gene expression by binding to specific DNA sequences known as estrogen response elements (EREs). Slight variations in the nucleotide composition of an ERE can affect the binding characteristics of ERs, which could ultimately affect the transcriptional rate of target genes. In addition, ERs are one of the most important nuclear hormone receptors in breast cancer biology. Therefore, there is a general need to develop a facile sensing technique to probe the interaction between estrogen receptor and DNA in order to discover new anti-cancer and gene regulation agents.

Example 1

Materials and Equipment

Hydrogen tetrachloroaureate(III) hydrate ($HAuCl_4 \cdot 3H_2O$) (99.99%) and trisodium citrate dihydrate (99.9%) were obtained from Aldrich Pte Ltd. Purified recombinant human estrogen receptors (ERα and ERβ were purchased from Pan Vera Corp (Madison, Wis.). Estrogen response element (ERE) oligonucleotides used in this study (refer to Table 1) were purchased from Sigma Pte Ltd (Singapore).

TABLE 1 estrogen response element (ERE) sequences used in the study

| Name (denoted as) | Sequence (from 5' to 3') |
|---|---|
| wild-type ERE (wtERE) | GTCCAAAGTCA<u>GGTCA</u>CAGT<u>GACC</u>TGATCAAAGT (Sequence ID No. 1) |
| mutant ERE (mutERE) | GTCCAAAGTCA<u>GTTCA</u>CAGT<u>GATC</u>TGATCAAAGT (Sequence ID No. 2) |
| non ERE (scrDNA) | GTCCAAAGTCAATCGCCAGCACGATGATCAAAGT (Sequence ID No. 3) |
| human pS2 ERE (pS2 ERE) | TCCCCCTGCAA<u>GGTCA</u>CGG<u>TGGCC</u>ACCCCGTGAG (Sequence ID No. 4) |

In Table 1, consensus ERE containing the optimal ERE core binding sequence (GGTCAnnnTGACC, n=spacer nucleotides (Sequence ID No. 5)) obtained from chicken vitellogenin gene is denoted as "wtERE", imperfect ERE sequence that contains base substitutions in the core is denoted as "mutERE", sequence scrambled DNA used as a negative control is denoted as "scrDNA", and natural sequence obtained from human is denoted as "pS2 ERE".

The two natural ERE sequences, i.e. wtERE and pS2 ERE differ from each other by only 1 base pair (shown in bold in Table 1) in the consensus core sequence. The synthetic mutated ERE sequence (mutERE) has two base substitutions to the consensus core sequence and is used as a control in the experiments.

Prior to use, the sense and antisense strands of DNAs were annealed in buffer solution (pH 7.4), comprising 10 mM tris-hydrochloric acid (tris-HCl), 100 mM sodium chloride (NaCl) and 1 mM ethylenediaminetetraacetic acid (EDTA), to form double-stranded ERE. All chemicals and materials were used as received without further purification. Ultrapure water (18 MO, prepared from Millipore Elix 3 purification system) was used as the solvent unless otherwise indicated.

Clear flat bottom UV-transparent microplates (96 well, Corning Incorporated, USA) were used as a reaction carrier. A TECAN infinite M200 plate reader (Tecan Trading AG, Switzerland) was used to measure the UV-vis absorption spectrum. A normal digital camera was used to record color of the solutions. Zeta potential measurements were performed on citrate-ion capped AuNPs in water, and wtERE, ERα, and ERα-ERE complex-coated AuNPs in buffer solution containing 20 mM KCl, using a ZETA PLUS zeta potential analyzer (Brookhaven Instruments, USA).

Example 2

Gold Nanoparticle (AuNP) Preparation

Gold nanoparticles (AuNPs) with an average diameter of about 13 nm were prepared by the citrate reduction of chloroauric acid ($HAuCl_4$). An aqueous solution of sodium citrate (5 mL, 40 mM) was added rapidly to a boiling solution (100° C.) of $HAuCl_4$ (50 mL, 1 mM). Within several minutes, color of the solution changed from pale yellow to red. The mixture was allowed to heat with stirring under reflux for 30 min to ensure complete reduction. The stirring was continued for an additional 15 min after removing the heating mantle and allowed to cool to room temperature.

Example 3

Determination of ERα-DNA Complex Formation

Sample solutions of (A') bare AuNPs (i.e. with no salt or biological molecules added), and AuNPs in the presence of (B) wtERE, (C) ERα and (D) ERα/wtERE complex were used in the experiments.

For (B), 50 nM of wtERE was added to a AuNP solution. For (C), 100 nM of ERα was added to a AuNP solution. For (D), ERα and wtERE were incubated in a molar ratio of 2:1 at room temperature for 30 min, in 10 mM Tris-HCl buffer solution (pH 7.4), comprising 80 mM potassium chloride (KCl), 0.15 mM EDTA, 0.3 mM dithiothreitol (DTT), and 1% of glycerol. Twenty-five microliters of the complex solutions was then mixed with 75 µL of the as-synthesized AuNPs to make up a final KCl concentration of 20 mM. The final concentrations of ERα and wtERE in the AuNP solution mixture were 100 nM and 50 nM respectively.

Figure 2:
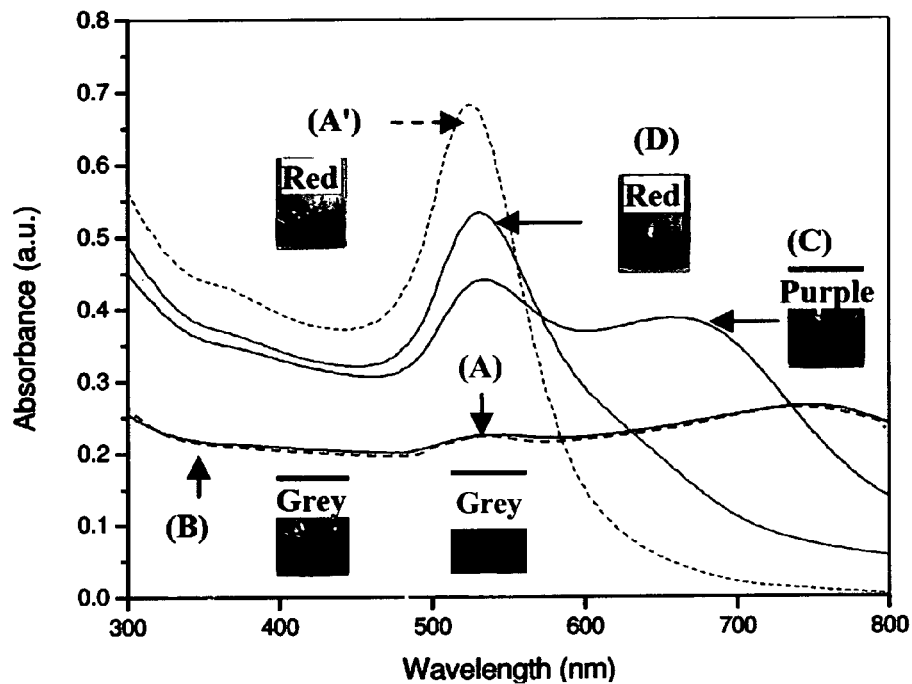
FIG. 2 is a graph showing UV-vis absorption spectra of AuNP samples (A'), and (A) to (D) recorded at 10 min upon addition of a salt solution of potassium chloride (KCl) to solutions (A) to (D) (final concentration of KCl in resultant solution at 20 mM). Sample (A') is a solution containing bare AuNPs (i.e. with no addition of salt or biomolecules), Sample (A) is a solution containing bare AuNPs (i.e. with no biomolecules) in salt solution, (B) is a solution containing AuNPs and 50 nM wtERE, (C) is a solution containing AuNPs and 100 nM ERα, and (D) is a solution containing AuNPs and ERα/wtERE complex (preincubated for 30 minutes in a buffer solution using 100 nM ERα and 50 nM wtERE). With reference to (A'), graph shows that absorbance peak value at wavelength=525 nm decreases with decreasing stability of solution. Insert of graph are photographs of the respective solutions taken 10 minutes after salt addition. Color of sample (D) is red, (C) is purple, which indicates that it is less stable compared to (D) and some precipitation of the AuNPs has occurred, and color of both sample (A) and (B) are grey, which indicates that the solutions are unstable, and precipitation of the AuNPs has occurred.

FIG. 2A is a graph showing the UV-vis absorption spectra of AuNP solutions (A'), and (A) to (D) recorded at 10 min upon addition of a salt solution of KCl to (A), (B), (C) and (D) (final concentration of KCl in resultant solution at 20 mM).

Sample (A') is used as the reference. A sharp surface plasmon peak is observed for curve (A') at 525 nm. All the three solutions with salt and biological sample (B) to (D) underwent distinct but different degrees of aggregation, characterized by color change associated with appearance of absorption at a longer wavelength (i.e. 650 nm) and the decrease of absorbance at 525 nm in their UV-vis absorption spectra. The degree of aggregation can refer to both the rate and the extent of aggregation of the AuNPs.

Sample (B) and (C) were not stable upon salt addition, as shown by a lower absorption level of about 0.23 and about 0.45 at a wavelength of 525 nm, compared to 0.67 for sample (A'), and a higher absorption level of about 0.24 and about 0.4 at a wavelength of 650 nm compared to 0.05 for sample (A'). Therefore, in terms of stability, sample (B) is the least stable of the three solutions, followed by sample (C) and sample (D), sample (D) being the most stable. Also shown are photographs of the respective solutions taken 10 minutes after salt addition. Color of sample (A') and (D) is red, which indicates that the solution is stable. Color of sample (C) is purple, which indicates that it is less stable compared to the sample (A) or (D), and some precipitation of the AuNPs has already taken place. Color of sample (B) is grey, which indicates that the solution is unstable, and precipitation of the AuNPs has occurred. This observation is consistent with the observations from the UV-vis graph in FIG. 2A.

Figure 3:
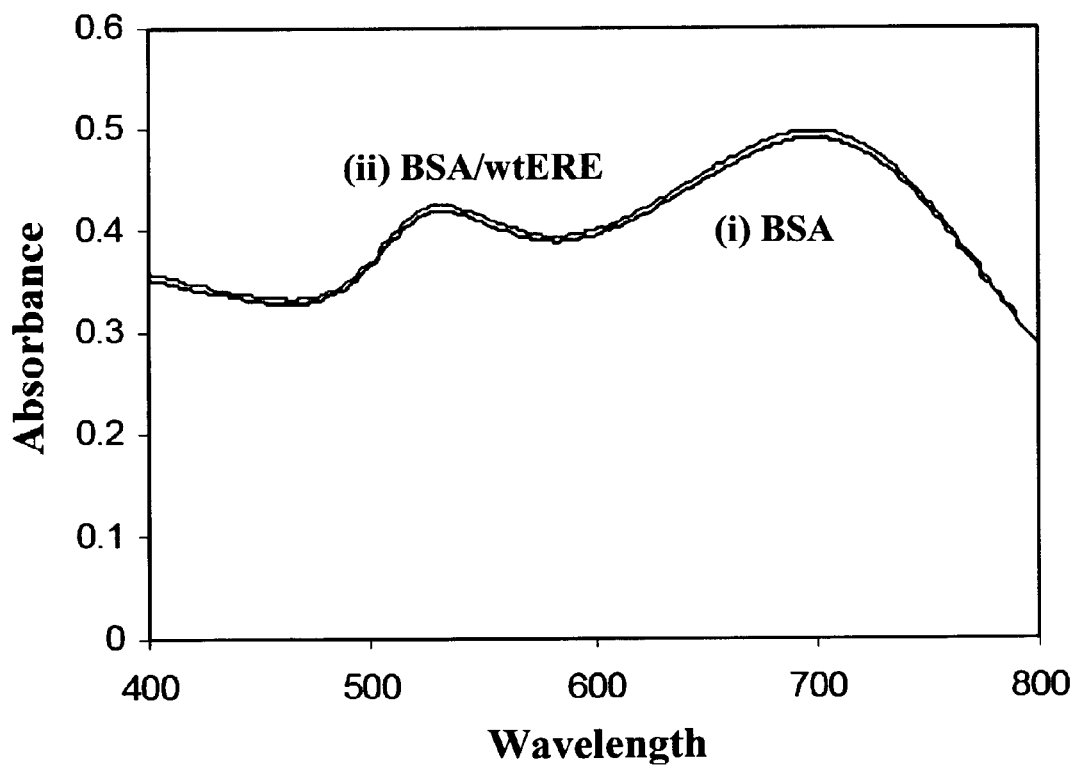
FIG. 3 is a graph showing UV-vis absorption spectra of AuNPs exposed to (i) bovine serum albumin (BSA) and (ii) BSA/wtERE mixture, taken at 10 minutes upon salt addition of KCl (final KCl concentration is 20 mM). No distinct difference in particle stability was observed from the graph upon salt addition to the AuNPs containing BSA or BSA/wtERE mixtures respectively. Also shown are photographs of the respective solutions taken 10 minutes after salt addition, in which the color of both solutions turned to blue.

A negative control experiment was carried out with bovine serum albumin (BSA) that has no specific binding to wtERE. BSA/wtERE was mixed in 10 mM tris-HCl buffer solution (pH 7.4), comprising 80 mM KCl, 0.15 mM EDTA, 0.3 mM DTT and 1% glycerol. FIG. 3 is a graph showing UV-vis of AuNPs exposed to (i) bovine serum albumin (BSA) and (ii) BSA/wtERE mixture, taken at 10 minutes upon salt addition of KCl (final KCl concentration is 20 mM). No distinct difference in particle stability was observed from the graph upon salt addition to the AuNPs containing BSA or BSA/wtERE mixtures respectively. Also shown are photographs of the respective solutions taken 10 minutes after salt addition. Both solutions were blue in color. This data further confirmed that sequence-dependent protein-DNA complex formation (ERα-ERE) is responsible for the higher particle stability.

Ratio of absorbance at wavelength of 650 nm to 525 nm (denoted as A650/A525) was used as a quantitative measure of the aggregation extent. FIG. 4 is a graph showing behavior of the ratio A650/A525 as a function of time. From the graph, it can be seen that the time at which gradient of the curve decreases is different among the tested samples, with sample (D) being the slowest, followed by sample (C), and sample (B). Therefore, AuNPs in the presence of ERα-wtERE complex i.e. sample (D) underwent the least and/or slowest aggregation upon salt addition, followed by sample (C), and lastly sample (B).

Without wishing to be bound by theory, the inventors of the present application believe that a nucleic acid, such as wtERE (which is a 34 base pair (bp) dsDNA) is unable to protect metallic nanoparticles, such as AuNPs, due to its double helical structure which exposes highly charged repulsive phosphate backbones. This highly charged repulsive backbone prevents nucleic acid bases, such as DNA bases from adsorption on the negatively charged metallic particle surface, such as AuNP surface. Consequently, no electrostatic protection is observed following addition of salt.

In the case of the example where ERα protein is the only constituent in the AuNP solution, the intermediate level of aggregation (blue color solution) may arise from both electrostatic and steric modulation. As ERα at the tested condition (pH 7.4) is slightly positively charged (isoelectric point of ERα is 8.333), the initial uptake of ERα would destabilize the negatively charged AuNPs due to charge neutralization. In addition, adsorption of this large 66 kDa protein may also provide a steric barrier to prevent the nanoparticles from crowding. It is well-known that some amino acids, for example cysteine (C) and histidine (H), show strong binding ability to noble metal via their functional side groups (e.g., thiol or imidazole). The absorption of ERα (13 C and 20 H out of 595 amino acids) onto AuNPs to provide steric protection can then be rationalized. FIG. 5 shows a ERα sequence. In the figure, the positively charged amino acid residues, i.e. hysine (K), histidine (H) and arginine (R) that may affect the charge property of the AuNPs are highlighted in grey. Cysteine (C) and H residues that could be responsible for the protein binding to AuNPs are underlined. The mutual compensation between these two effects (electrostatic destabilization and steric stabilization) eventually leads to the intermediate particle stability observed.

In contrast, the low AuNP aggregation found when exposed to the ERα-wtERE complex could be attributable primarily to the larger molecular size of the complex (ERα binds ERE as a dimer), providing a more effective steric protection compared with ERα. Additionally, the coating of ERα-wtERE complex on the AuNP surface (through the protein's amino acid side groups) may also allow AuNPs to gain more electrostatic protection due to the presence of heavily charged wtERE in the complex.

Example 4

Characterisation Using Zeta Potential Measurement

FIG. 6 is a graph comparing zeta potential of sample (A') bare AuNPs (without salt addition), (B) wtERE, (C) ERα, and (D) ERα/wtERE, which are prepared in salt solution according to the procedure outlined in Example 3. The zeta potential of sample (A') to (D) is (−32.82±2.43 mV), (−11.29±5.65 mV), (−10.55±4.90 mV) and (−24.04±6.45 mV) respectively.

Sample (B) comprises wtERE, which is a 34 bp dsDNA, is unable to protect or shield AuNPs due to its double helical structure which exposes highly charged repulsive phosphate backbones. Therefore, wtERE is not able to adsorb on the negatively charged AuNPs surface. Consequently, the AuNPs are not stabilized, and no electrostatic protection is observed following addition of salt, and which is seen by the much lower zeta potential value of (−11.29±5.65 mV) compared to that for bare AuNPs of (−32.82±2.43 mV).

For sample (C) comprising ERα protein, intermediate level of aggregation (purple color solution) may arise from both electrostatic and steric modulation. As ERα at the tested condition of pH 7.4 is slightly positively charged (isoelectric point of ERα is 8.333), the initial uptake of ERα would destabilize the negatively charged AuNPs due to charge neutralization. Moreover, the absorption of this large 66 kDa protein may also provide a steric barrier to prevent the nanoparticles from crowding. The relatively low surface charge as shown by the zeta potential of (−10.55±4.90 mV) measured for the ERα-coated AuNPs confirms the charge neutralization and that the steric protection is attributable to the immediate stability.

In contrast, the low AuNPs aggregation found when exposed to ERα-wtERE complex in sample (D) could be attributable primarily to the larger molecular size of the complex (ERα binds ERE as a dimer), providing a more effective steric protection compared with ERα. Additionally, the coating of ERα-wtERE complex on the AuNPs surface, which can take place through the protein's amino acid side groups, may also allow AuNPs to gain more electrostatic protection due to the presence of heavily charged wtERE in the complex. The higher negative charge density measured by the zeta potential (−24.04±6.45 mV) confirms this. The protection from both electrostatic effect and steric effect is attributable to the significantly improved salt stability exerted by the ERα-wtERE complex.

Also shown are photographs of Sample (B) wtERE, (C) ERα, and (D) ERα/wtERE taken 10 minutes after salt addition (final KCl concentration of 20 mM).

Example 5

Determination of ERα-DNA Binding Stoichiometry

Figure 7A:
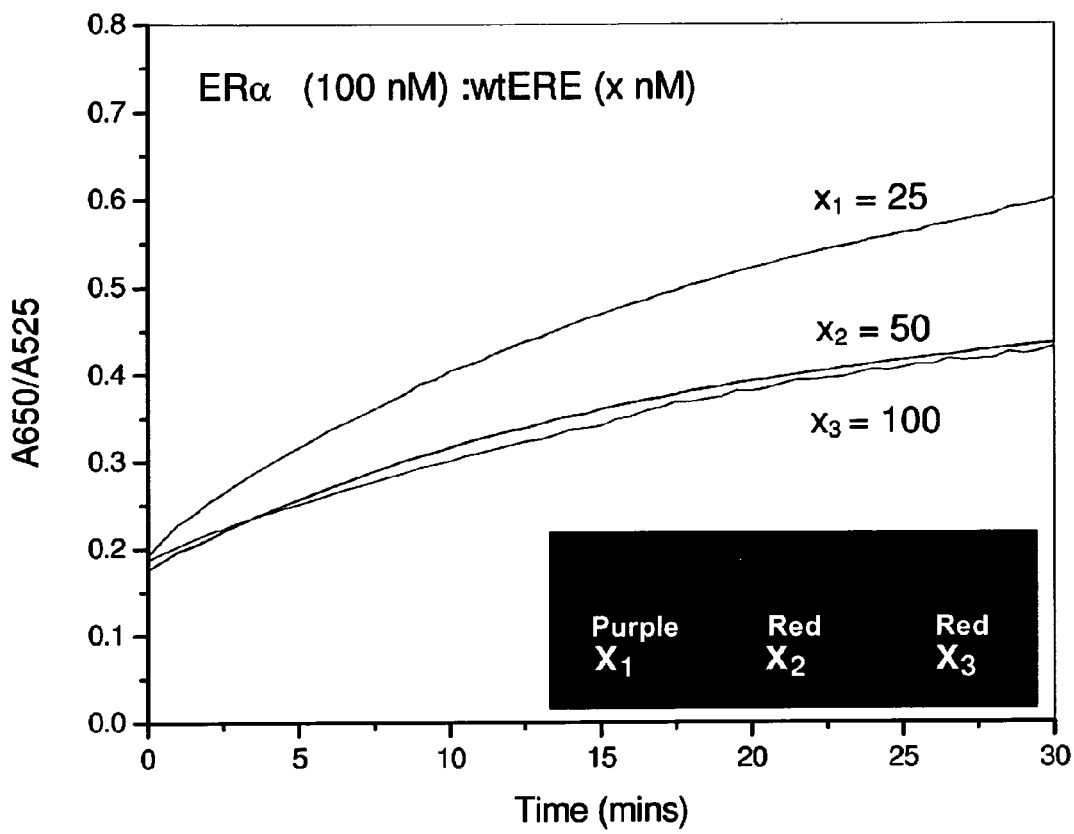
FIG. 7A is a graph showing A650/A525 versus time of AuNPs exposed to different concentrations of ERE. It can be seen that particle stability was low when a small amount of 25 nM ERE was used, as the ERE used was insufficient to complex with the ERα present. When the ERE amount was increased to 50 nM and 100 nM, stability of AuNPs increased. However, increasing the wtERE concentration from 50 nM to 100 nM did not result in further improvement in stability of AuNPs, as no further ERα was available to form more complexes. This is consistent with the finding that ERα binds to wtERE as a dimer.

To determine the binding stoichiometry of ERα-wtERE complex formation, 100 nM ERα was incubated with a varied amount of wtERE (denoted by x, in which $x_1=25$, $x_2=50$, and $x_3=100$ nM) before testing. FIG. 7A is a graph showing A650/A525 versus time. It can be seen that particle stability was low when a small amount of 25 nM ERE was used, as the ERE used was insufficient to complex with the ERα present. When the ERE amount was increased to 50 nM and 100 nM, stability of AuNPs increased. This further confirms that amount of protein-DNA complex is associated with stability of AuNPs and inhibition of nanoparticle aggregation.

In addition, as shown in FIG. 7A, increasing the wtERE concentration to 100 nM did not result in further improvement in stability of AuNPs, as no further ERα was available to form more complexes, given that molar ratio of ERα-wtERE is 2:1 (i.e. 100 nM to 50 nM). This is consistent with the finding that ERα binds to wtERE as a dimer, as characterized using SPR and fluorescent anisotropy techniques. This approach to unravel protein-DNA binding stoichiometry is more convenient than using surface plasmon resonance (SPR) spectroscopy that relies on titration of a known amount of immobilized DNA with increasing protein concentrations to determine amount of protein that saturates the DNA.

Example 6

Determination of ERα-DNA Binding Sequence Specificity

The inventors have further demonstrated that the method of determining protein-nucleic acid interaction according an embodiment of the present invention could be used to screen for impact of sequence variation on protein-DNA binding affinity. Besides wtERE that contains a perfect core ERE sequence, a mutant ERE (mutERE) with two base substitutions in the core and a negative control DNA (scrDNA) with the entire core sequence randomly scrambled was used (refer to Table 1). The mutERE is known to have a very low protein binding affinity compared to wtERE, whereas the scrDNA has no sequence-dependent binding to the receptor but exerts weak electrostatic contact. Each individual sequence (50 nM) was pre-incubated (for 30 min) with the receptor (100 nM). The use of an ERR-ERE ratio of 2:1 was to ensure the formation of fully saturated ERR-DNA complexes according to the binding stoichiometry previously determined. Colorimetric testing was then carried out for each of the samples in the AuNP solution.

Figure 7B:
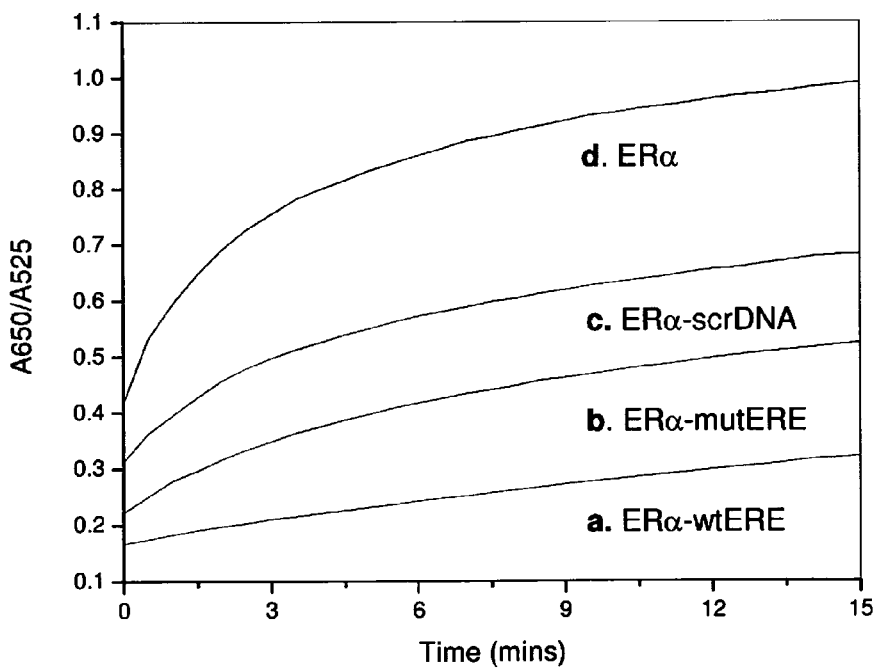
FIG. 7B is a graph showing A650/A525 versus time of sample (a) ERα-wtERE, (b) ERα-mutERE, (c) ERα-scrDNA, and (d) ERα. All the complexes were pre-incubated at ERα-ERE ratio of 2:1 (i.e. 100 nM:50 nM) before subjecting to colorimetric testing.
Figure 7C:
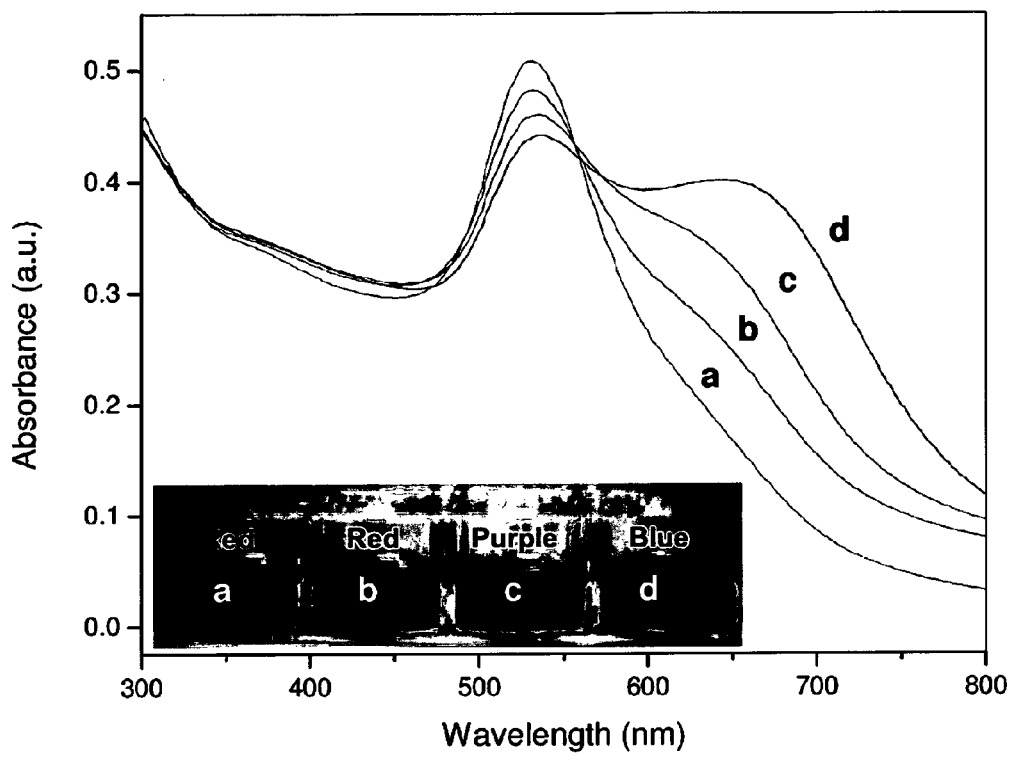
FIG. 7C is a graph showing UV-vis absorption spectra, as well as a photograph of samples (a) to (d), which are taken at 15 minutes upon addition of KCl (final concentration of 20 mM) to trigger particle aggregation. Photograph shows that the color of sample (a) and (b) are red, (c) is purple and (d) is blue.

FIG. 7B is a graph of A650/A525 versus time showing the aggregation kinetics. FIG. 7C is a graph showing the endpoint UV-vis absorption spectra taken at 15 min upon salt addition, as well as photographs depicting solution color of AuNPs exposed to ERα complexes with the respective DNA sequences of (a) wtERE, (b) mutERE, and (c) scrDNA. Sample (d) is ERα in the absence of target DNA, which was used as a control.

Degree of stabilization exerted by different ERα-DNA complexes was found to be sequence-dependent, following the affinity order of ERα-wtERE>ERα-mutERE>ERα-scrDNA, with ERα-wtERE the highest affinity. Perfect ERE sequence (wtERE) bind with highest affinity to ERα whereas imperfect ERE sequences differing by one or more nucleotides are known to decrease the binding affinity to ERα. This affinity order was also observed using techniques such as SPR.

Without wishing to be bound by theory, the inventors believe that correlation between binding affinity of protein-nucleic acid complex, such as ER-ERE complex, and stability of metallic nanoparticles, such as AuNP, can be stated as, the higher the binding affinity, the better the electrosteric protection conferred by the protein-nucleic acid complex. Steric effects exerted by the protein-nucleic acid complexes are dominantly responsible for the stabilization of the metallic nanoparticles. Thus the efficiency of complex formation, i.e. the amount of protein-nucleic acid complex formed, will determine the particle stability. For example, as illustrated herein, when the ERE core is mutated, contact between the protein and DNA is disrupted, leading to a weaker binding interaction and inefficient ERα/DNA complexation. This would reduce the amount of complexes formed; as such the degree of aggregation is greater relative to the case with more effective complexation with the wild-type ERE.

In particular, the inventors have observed that this stability order is consistent throughout the kinetics measurement over 15 min. Therefore, by maintaining a same sampling time for all samples upon salt addition, a shorter monitoring period, such as 1 minute for example, can be used for a fast colorimetric detection.

Example 7

Generality to Other Protein Subtype: ERβ-ERE Complex Formation, Stoichiometry, and Sequence Specificity To demonstrate generality of the current assay, similar experiments were carried out for ERβ, which is another protein subtype that has a high degree of homology (96% amino acid identity). Even though ERβ has ERα in its DNA binding domain, however, it harbors a distinct DNA binding profile. Specifically, estrogen-bound ER/3 binds to consensus ERE sequence at a higher order than ERα with a weaker binding affinity.

Figure 8A:
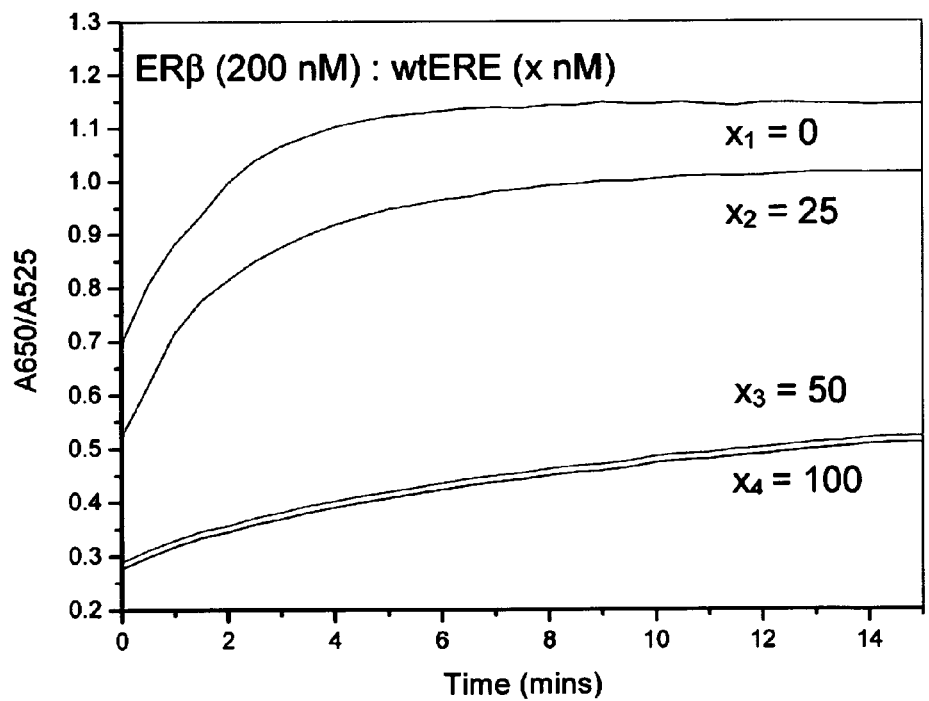
FIG. 8A is a graph showing A650/A525 versus time of AuNPs exposed to an ERβ-wtERE incubation mixture of 200 nM ERβ, with various amounts of wtERE (denoted by x, in which $x_1$=0, $x_2$=25, $x_3$=50, and $x_4$=100 nM). When the ERE amount was increased to 50 nM and 100 nM, stability of AuNPs increased. However, increasing the wtERE concentration from 50 nM to 100 nM did not result in further improvement in stability of AuNPs, as no further ERβ was available to form more complexes. This is consistent with the finding that ERβ binds to wtERE as a tetramer.

The method of determining protein-nucleic acid interaction according to an embodiment of the present invention was used to detect formation of ERβ-wtERE complex, and to determine the binding ratio of ERβ to wtERE in forming fully saturated complex. FIG. 8A is a graph showing A650/A525 versus time of AuNPs exposed to an ERβ-wtERE incubation mixture of 200 nM ERβ, with various amounts of wtERE (denoted by x, in which $x_1=0$, $x_2=25$, $x_3=50$, and $x_4=100$ nM).

Results show that the formation of an ERβ-wtERE complex is detectable by the improved particle stability, relative to the case with ERβ only. Moreover, at an ERβ-wtERE ratio of 4:1, stability of AuNPs is maximized, thereby indicating that ERβ was completely consumed at this condition. This result suggests that ER/3 binds to wtERE as a tetramer, which has been previously reported using SPR spectroscopy and fluorescence anisotropy. This validates the utility of this AuNP-based colorimetric assay. This experimentally determined binding ratio (4:1 of ERβ-wtERE) was then used as an incubation condition in the next series of experiments.

Figure 8B:
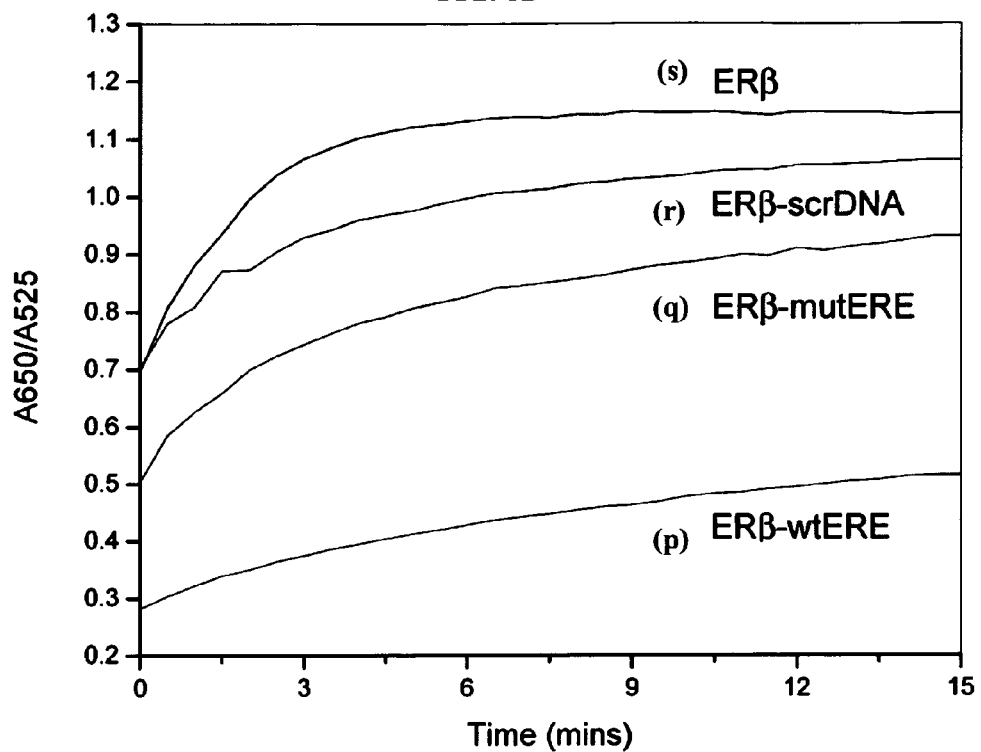
FIG. 8B is a graph showing A650/A525 versus time of sample (p) ERβ-wtERE, (q) ERβ-mutERE, (r) ERβ-scrDNA, and (s) ERβ. Sample (s) was used as a control. All the complexes were pre-incubated at ERβ-ERE ratio of 4:1 (i.e. 200 nM:50 nM) before subjecting to colorimetric testing.
Figure 8C:
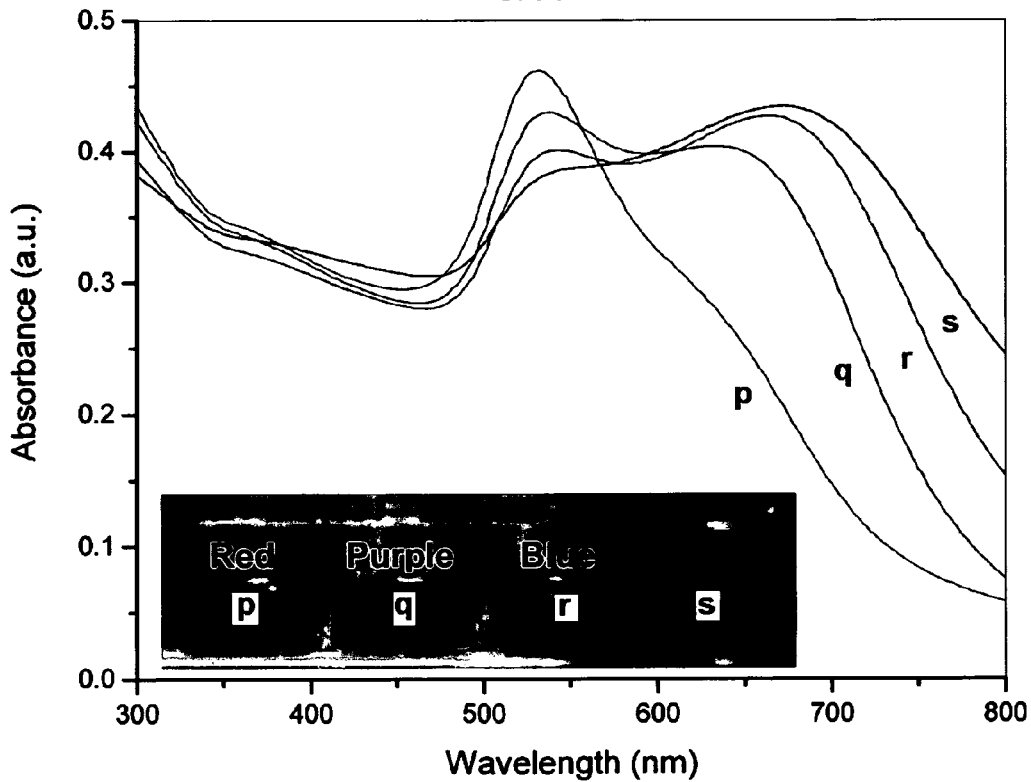
FIG. 8C is a graph showing UV vis spectra of samples (p) to (s), which are taken at 15 minutes upon salt addition of KCl (final concentration of 20 mM), which was used to trigger particle aggregation.

FIG. 8B is a graph showing A650/A525 versus time of sample (p) ER/3-wtERE, (q) ERβ-mutERE, (r) ERβ-scrDNA, and (s) ERβ. Sample (s) was used as a control. All the complexes were pre-incubated at ERβ-ERE ratio of 4:1 (i.e. 200 nM:50 nM) before subjecting to colorimetric testing. FIG. 8C is a graph showing UV vis spectra of samples (p) to (s), which are taken at 15 minutes upon salt addition of KCl (final concentration of 20 mM), which was used to trigger particle aggregation.

As can be seen from FIGS. 8B and 8C, AuNPs protected by ERβ-DNA complexes are more stable than those protected by ERβ alone. The stabilization effect is in the order of ERβ-wtERE>ERβ-mutERE>ERβ-scrDNA, with ERβ-wtERE having the highest stability, thereby corresponding well with results obtained through SPR. This result, together with that for ERα, are evidence that the method of determining protein-nucleic interaction according to an embodiment of the invention is reliable and sensitive to determine the relative binding affinities of a protein to different DNA sequences.

In addition, incubation mixtures of ERα and ERβ with the scrambled DNA (no specific core sequence for the receptors) have been shown to stabilize the nanoparticles (Curves (r) in FIG. 7B and FIG. 8B) better than using the receptors alone, which proves that this assay is capable of measuring weak and transient protein-DNA binding that is usually difficult to detect in using techniques such as electrophoretic mobility shift assay (EMSA).

Example 8

Determination of Sequence Specificity with Single Base-Pair Resolution

To further demonstrate capability of the current assay to detect subtle differences in protein binding affinity introduced by a single base substitution, experiments were carried out on another natural-occurring ERE sequence (i.e., human pS2 ERE), which differs from the wtERE by only one base pair (bold, refer to Table 1) in its core sequence. Using solid-liquid phase SPR measurements, it was previously determined that the binding affinity of ERα to pS2 ERE is only 18% less than its binding to wtERE (see for example, Teh, H. F. et al., J. S. Biochemistry 2007, 46, 2127-2135). This difference is much smaller than that seen using the mutERE (about 60%) containing a two-base pair substitution.

Figure 9A:
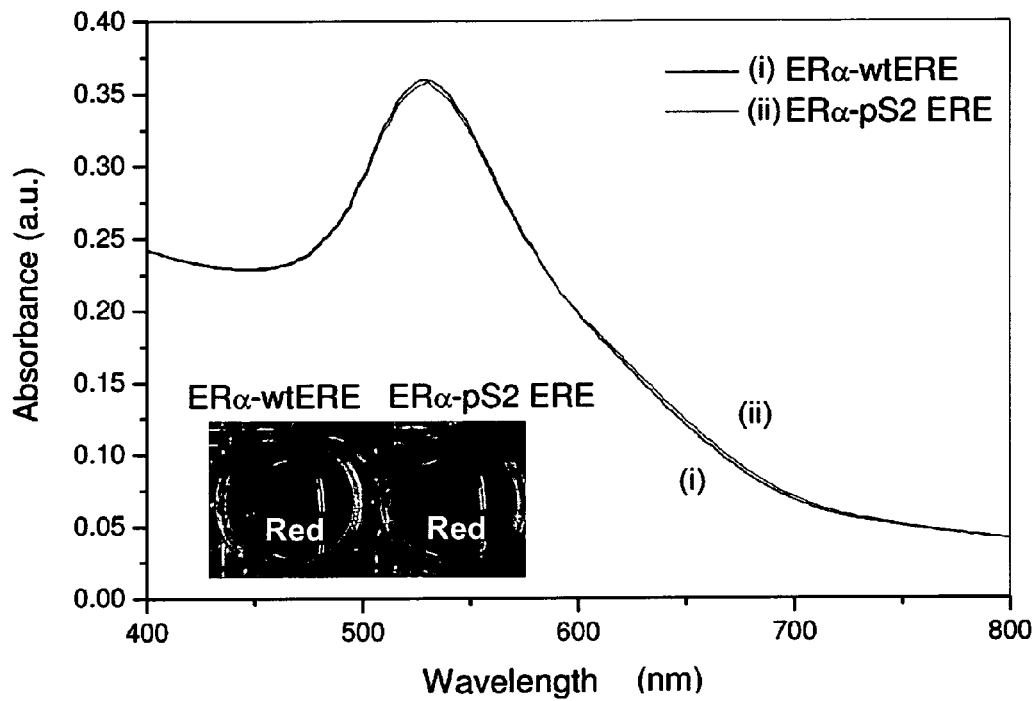
FIG. 9A is a graph showing UV vis spectra of AuNPs exposed to ERα-wtERE complex and ERα-ps 2 ERE complex. The ERα to ERE ratio used was 2:1. A final salt concentration of 20 nM KCl was used to induce particle aggregation, which is the same amount used in previous experiments for ERE sequences having more base substitutions.
Figure 9B:
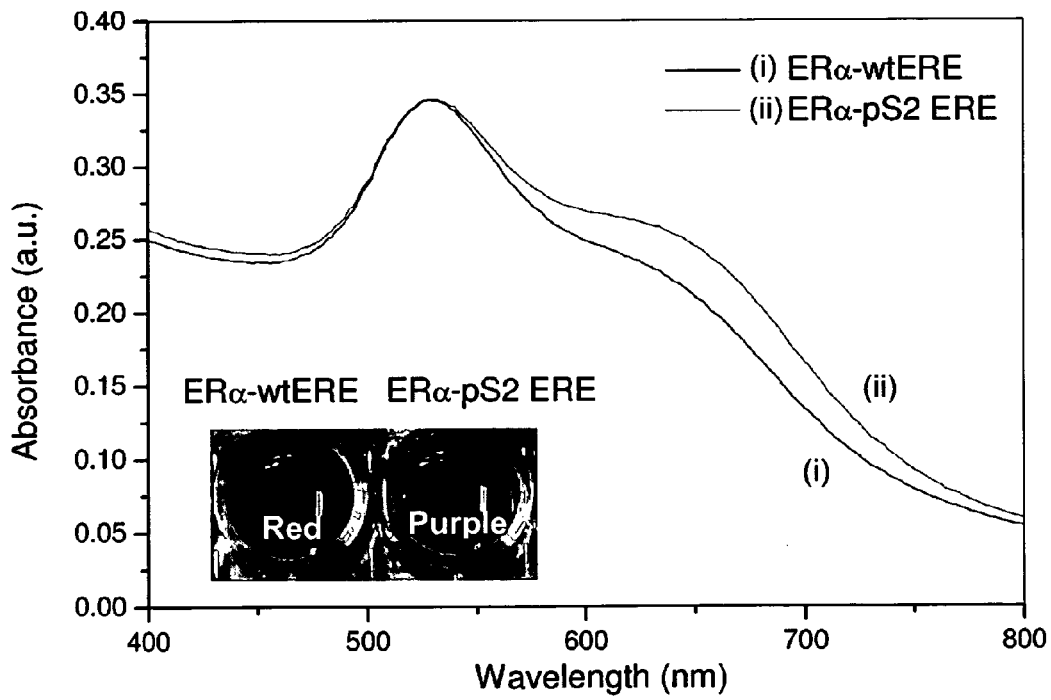
FIG. 9B is a graph showing UV vis spectra of ERα-wtERE complex and ERα-ps 2 ERE complex. The ERα to ERE ratio used was 2:1. A final salt concentration of 50 nM KCl was used to induce particle aggregation.

FIG. 9A is a graph showing UV vis spectra of ERα-wtERE complex and ERα-ps 2 ERE complex. The ERα to ERE ratio used was 2:1. A final salt concentration of 20 nM KCl was used to induce particle aggregation, which is the same amount used in previous experiments for ERE sequences having more base substitutions. From the graph, it appears that the difference in ERα binding affinity between the very similar wtERE and pS2 ERE sequences did not appear to show up as well as previous experimental results described herein. FIG. 9B is a graph showing UV vis spectra of ERα-wtERE complex and ERα-ps 2 ERE complex. The ERα to ERE ratio used was 2:1. A final salt concentration of 50 nM KCl was used to induce particle aggregation. From the graph, it can be seen that when the final salt concentration of KCl was increased from 20 mM to 50 mM to provide a more stringent condition for AuNP aggregation, there is a discernible difference in ERα binding affinity between the very similar wtERE and pS2 ERE sequences. Therefore, using this spectrum shift, the amount of salt required to induce particle aggregation can be determined. The particle solution containing the ERα-pS2 ERE incubation mixture is 19% less stable than that containing ERR-wtERE, as measured by the absorbance difference at wavelength λ650. These results demonstrate that upon a proper optimization of assay conditions, the current AuNP-based colorimetric assay is amendable for the detection of protein-DNA binding specificity up to a single nucleotide resolution.

Example 9

Solid-Liquid Phase Surface Plasmon Resonance (SPR) Experiments

To address the concern of the compatibility of the complex formation and colorimetric detection conditions, solid-liquid phase SPR experiments were conducted. FIG. 10 is a SPR sensorgram showing the binding of ERα (prepared in Tris-HCl buffer solution containing 80 mM KCl, 0.15 mM EDTA, 0.3 mM DTT and 1% of glycerol) to the immobilized ERα-wtERE on gold chip, followed by exchanges between protein binding buffer and AuNPs aggregation buffers. The down arrows indicate the time when the surface is rinsed with the protein binding buffer (80 mM KCl). The dash arrows indicate the time when diluted buffer containing low concentration of KCl (20 or 50 mM KCl) is applied. From the graph, a reversible buffer effect due to bulk refractive index change was observed. However, there is no dissociation of bound protein as the binding signal goes back to the same level when the binding buffer was applied (refer to dashed line on the graph). This confirms compatibility of buffer conditions used for protein-DNA complex formation and colorimetric detection. Therefore, the protein-DNA complex formed in binding buffer remains stable when exposed to aggregation buffer solutions. The SPR results confirm that ERα-DNA complexes performed under physiological salt conditions (addition of 80 mM KCl, in which the ERα-DNA complexes are maintained in solution through multiple hydrogen bonds and van der Waals forces) remain stable when exposed to the diluted buffer containing a low concentration of KCl at 50 mM, or a lower concentration of KCl at 20 nM.

Example 10

Generality to Other Protein DNA Binding System

This assay principle is further validated with single-stranded DNA binding protein (SSB) and one of the strands of the wtERE. FIG. 11 is a graph showing UV-vis spectra of AuNPs exposed to SSB, SSB-ss(wtERE) and ss(wtERE). AuNPs in the presence of SSB-ssDNA complex was able to withstand the salt-induced aggregation due to their larger molecular size and richer charge compared with SSB or ssDNA alone. These results show that the method to determine protein-nucleic acid interaction according to an embodiment of the present invention is generic to detect the formation of protein-DNA complex, especially for those protein-DNA binding systems where the resulted complexes have significantly larger molecular size (when protein binds DNA at higher orders, like dimer) and distinguishable charge properties relative to DNA and protein before forming complexes.

What is claimed is:

1. A method of determining protein-nucleic acid complex formation, wherein the method comprises:
mixing a nuclear hormone receptor protein with a sample comprising a double stranded nucleic acid which is suspected to form a complex with the protein to form a first mixture;
adding metallic nanoparticles with a negative surface charge to the first mixture to obtain a second mixture;
adding an electrolyte to the first or second mixture; and
determining the protein-nucleic acid complex formation from assessing a difference in degree of aggregation of metallic nanoparticles in the second mixture before and after addition of the electrolyte.

2. The method of claim 1, wherein the metallic nanoparticles are dispersed in the first mixture.

3. The method of claim 1, wherein the metallic nanoparticles are noble metal nanoparticles.

4. The method of claim 3, wherein the noble metal nanoparticle are made of a noble metal selected from the group consisting of silver, gold and alloys of the aforementioned materials.

5. The method of claim 1, wherein the metallic nanoparticles each have a size in at least one dimension in a range of between about 10 nm to about 900 nm.

6. The method of claim 5, wherein the metallic nanoparticles each have a size in at least one dimension in a range of between about 10 nm to 50 nm.

7. The method of claim 1, wherein the metallic nanoparticles have a shape which is selected from the group consisting of a nanosphere, a nanocube, a nanorod, a nanotube, a nanostar, a nanocrescent, a nanoplate and mixtures thereof.

8. The method of claim 1, wherein the negative charge of the metallic nanoparticles is conferred by a carboxylic acid or sulfonic acid or carbolic acid or a mixture thereof immobilized at the surface of each of the metallic nanoparticles.

9. The method of claim 8, wherein the carboxylic acid is selected from the group consisting of citric acid, lactic acid, acetic acid, formic acid, oxalic acid, uric acid, pyrenedodecanoic acid, mercaptosuccinic acid, and aspartic acid.

10. The method of claim 1, wherein the nucleic acid is selected from the group consisting of DNA, RNA, and DNA-RNA hybrid.

11. The method of claim 1, wherein the protein-nucleic acid complex formation is determined by measuring the optical properties of the metallic nanoparticles or the size of the metallic nanoparticle aggregates.

12. The method of claim 1, wherein the binding efficiency of the protein-nucleic acid complex formation is determined by correlating the optical properties of the metallic nanoparticles or the size of metallic nanoparticle aggregates in one sample with the optical properties or size of metallic nanoparticle aggregates of another sample, wherein the other sample comprises a known sequence-specific nucleic acid binding to said protein with high affinity.

13. The method of claim 11, wherein the optical properties are determined with the naked eye or with a spectrophotometer.

14. The method of claim 1, wherein the electrolyte is a salt.

15. The method of claim 1, wherein the salt is an organic salt or an inorganic salt.

16. The method of claim 15, wherein the concentration of the salt is between about 0.01 to about 0.5 M.

17. The method of claim 1, wherein the nuclear hormone receptor is selected from the group consisting of estrogen receptor (ER), thyroid hormone receptor (TR), vitamin D receptor (VDR), retinoic acid receptor (RAR), retinoid X receptor (RXR), progesterone receptor (PR), androgen receptor (AR), glucocorticoid receptor (GR), mineralcorticoid receptor (MR), and peroxisome proliferation-activated receptor (PPAR).

18. The method of claim 1, wherein assessing a difference in degree of aggregation of metallic nanoparticles in the second mixture before and after addition of the electrolyte comprises determining if the degree of aggregation of metallic nanoparticles in the second mixture after addition of the electrolyte has increased, whereby such an increase indicates an absence of the double stranded nucleic acid which is suspected to form a complex with the protein.

* * * * *